United States Patent
Sasai

(10) Patent No.: US 8,301,460 B2
(45) Date of Patent: Oct. 30, 2012

(54) INFORMATION PRESENTATION SYSTEM, COMPUTER PROGRAM, AND COMPUTER SOFTWARE PRODUCT

(75) Inventor: Kosuke Sasai, Kobe (JP)

(73) Assignee: Konica Minolta Medical & Graphic Inc., Tokyo (JP)

( * ) Notice: Subject to any disclaimer, the term of this patent is extended or adjusted under 35 U.S.C. 154(b) by 873 days.

(21) Appl. No.: 11/653,799

(22) Filed: Jan. 16, 2007

(65) Prior Publication Data

US 2007/0168231 A1    Jul. 19, 2007

(30) Foreign Application Priority Data

Jan. 17, 2006  (JP) .................................. 2006-008327

(51) Int. Cl.
*G06Q 50/00*     (2012.01)
(52) U.S. Cl. ............................................. 705/2; 705/3
(58) Field of Classification Search .................... 705/2–3
See application file for complete search history.

(56) References Cited

U.S. PATENT DOCUMENTS

| | | | |
|---|---|---|---|
| 2003/0216939 A1* | 11/2003 | Bito et al. | 705/2 |
| 2004/0186745 A1* | 9/2004 | Funahashi | 705/2 |
| 2006/0059012 A1* | 3/2006 | Thompson | 705/2 |

FOREIGN PATENT DOCUMENTS

| | | | |
|---|---|---|---|
| JP | 2005-004260 | | 1/2005 |
| JP | 2005-004260 | * | 6/2005 |

* cited by examiner

*Primary Examiner* — Sind Phongsvirajati
(74) *Attorney, Agent, or Firm* — Brinks Hofer Gilson & Lione

(57) ABSTRACT

Associated information is prepared and stored in a support information DB, the information being such that elements belonging to a plurality of element items respectively forming medical information on at least one patient are associated with each other between the items. Then, on a medical-support-information presenting screen displayed at a display unit, a selecting condition selecting one or more elements and an output target item are specified and input in response to user control. As a result, with respect to information that satisfies the selecting condition out of the associated information, the display unit visibly outputs statistical information about the output target item.

20 Claims, 22 Drawing Sheets

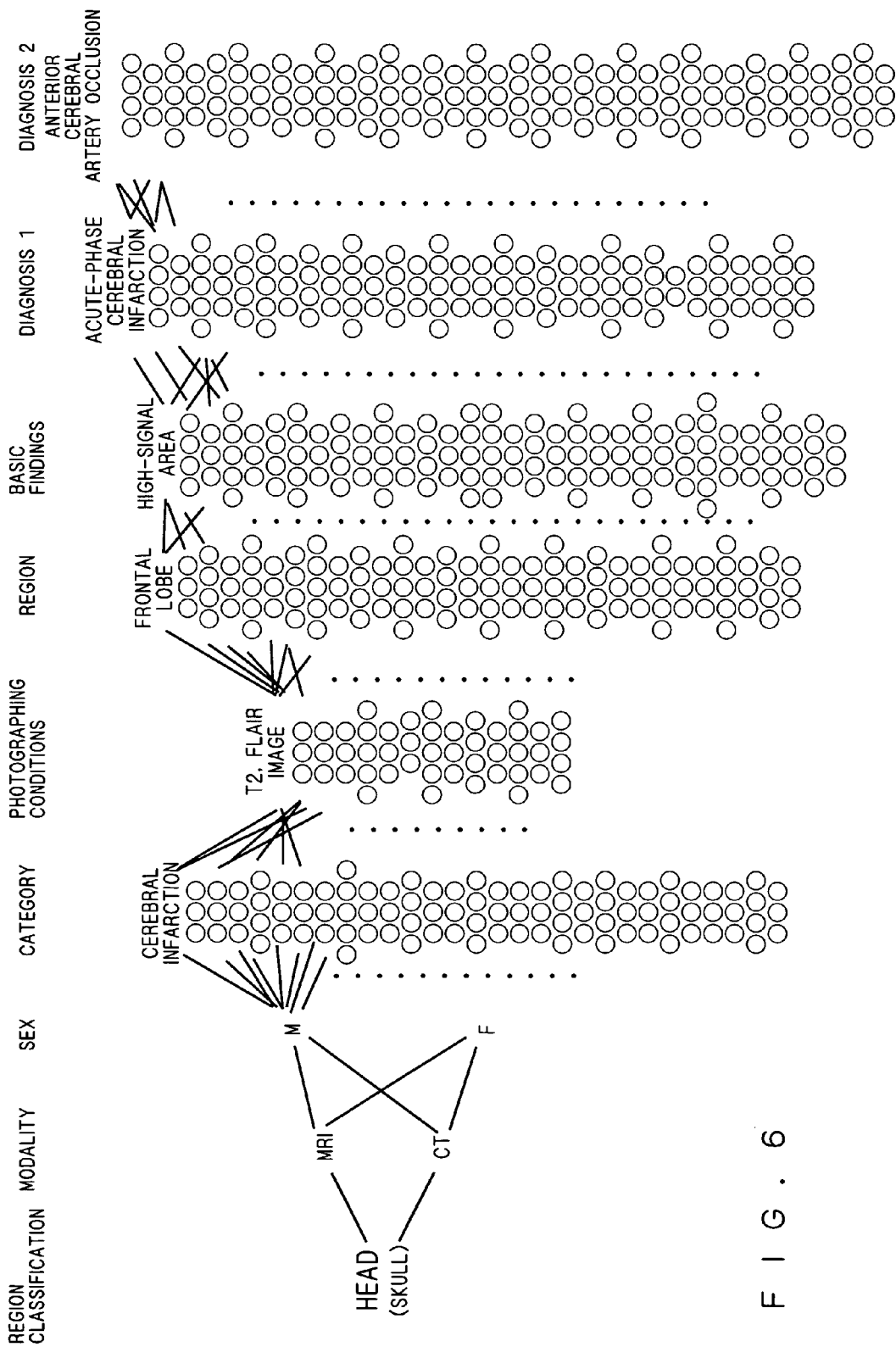
F I G. 6

| BLOOD TEST RESULT | STOMACH CANCER | ← A11

LIPID
CARBOHYDRATE METABOLISM
LIVER FUNCTION
RENAL FUNCTION
INFLAMMATION
ANAEMIA
TUMOR MARKER
  CEA
  AFP
  CA-19-9
↙ A13

MP ↘

| REGION | SIZE | METASTASIS TO LYMPH NODE |

GASTRIC ANGLE — <1cm — 0/10
CORPUS VENTRICULI — 1-2cm — 1-2/10
STOMACH FUNDUS — 2-3cm — 2-3/10
PYLORUS — 3-4cm — 3-4/10
CARDIAC ORIFICE — 4cm< — 5/10<

F1  F2  A12  F3

NO FINDINGS / RELEVANT SYMPTOM ← DD2

F I G . 1 5
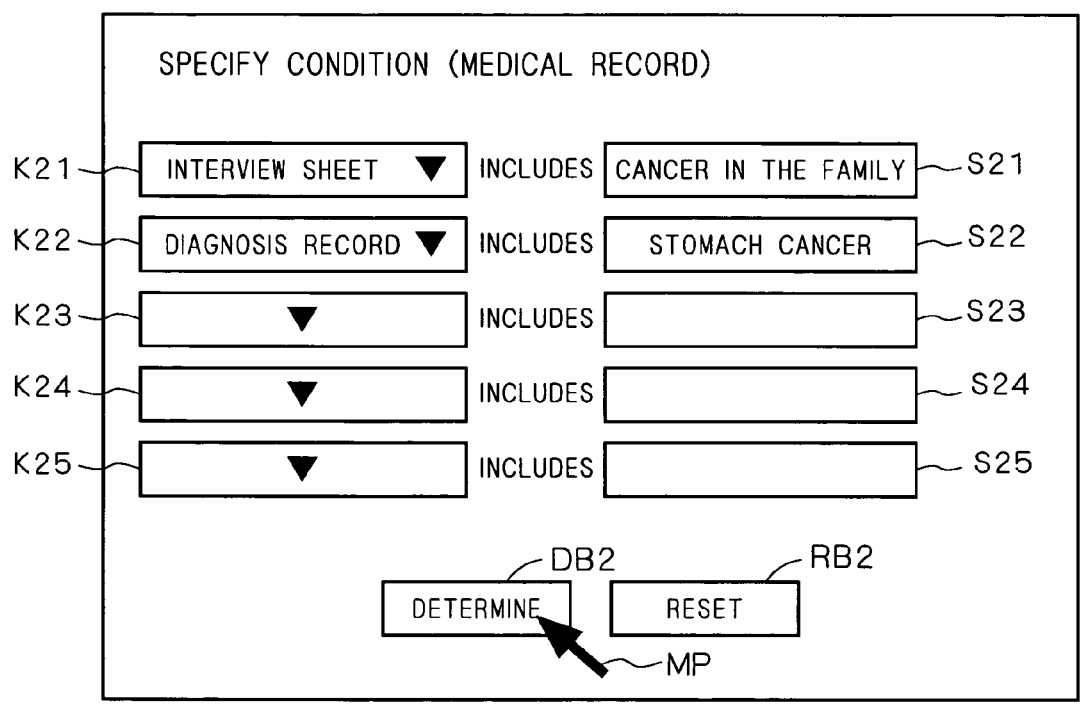

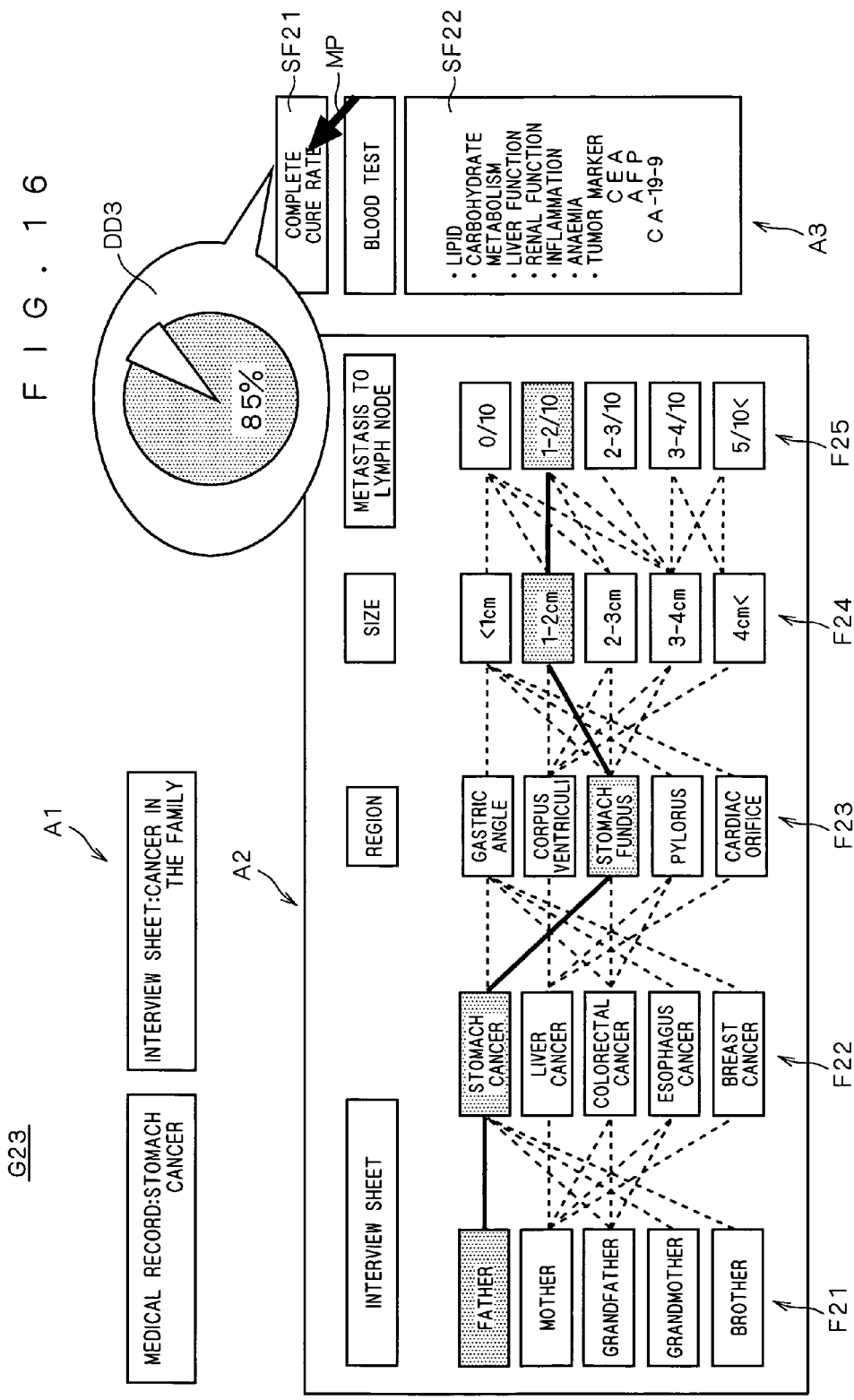

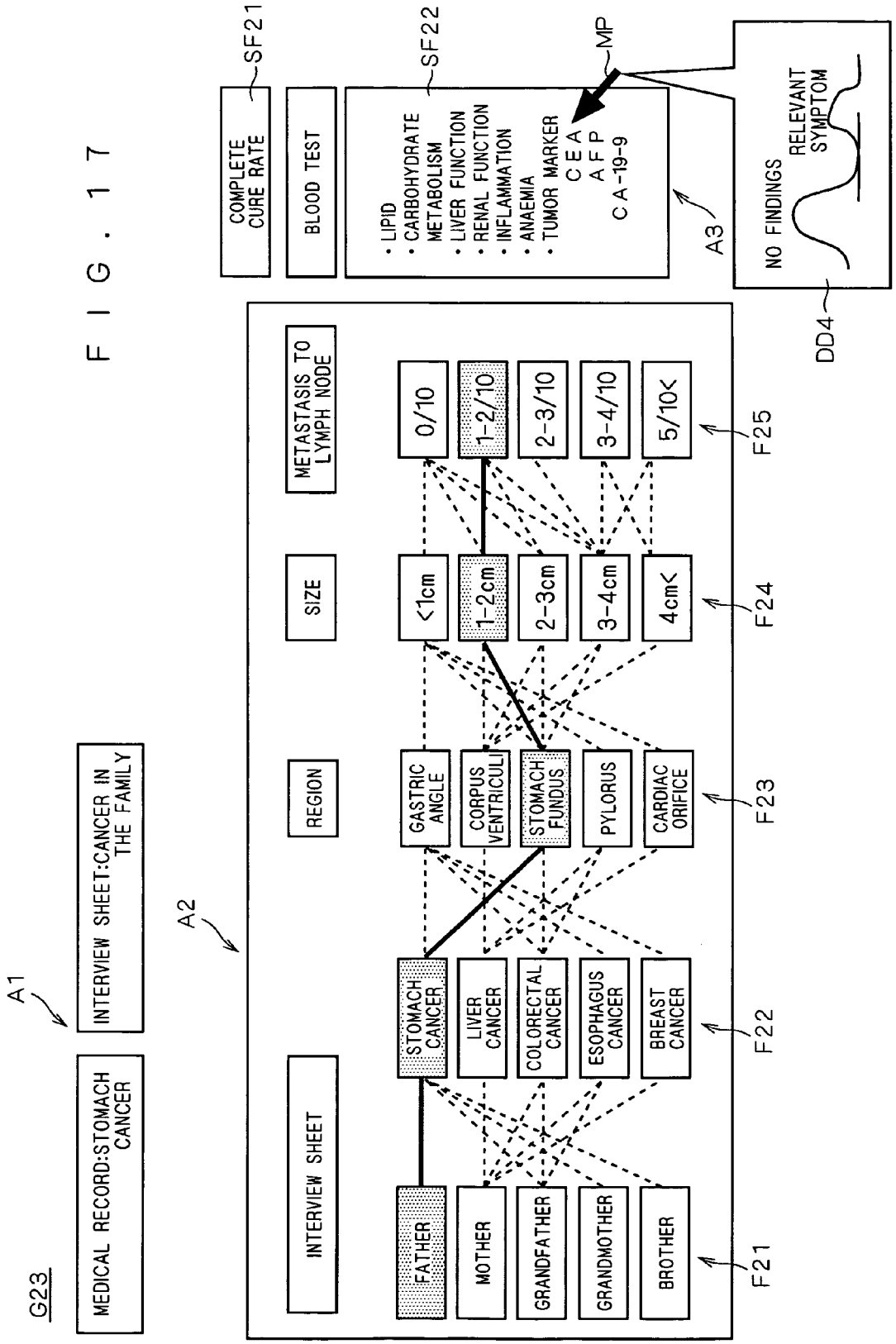

INFORMATION PRESENTATION SYSTEM, COMPUTER PROGRAM, AND COMPUTER SOFTWARE PRODUCT

This application is based on application No. 2006-008327 filed in Japan, the contents of which are hereby incorporated by reference.

BACKGROUND OF THE INVENTION

1. Field of the Invention

The present invention relates to a system for presenting information.

2. Description of the Background Art

In recent years, medical institutions such as hospitals have introduced a system for managing various kinds of medical information as electronic data (information management system) including electronic charts.

This system includes a subsystem for each department, to manage various kinds of medical information such as electronic charts and blood test results on a subsystem-by-subsystem basis.

A technique has also been disclosed for statistically processing and presenting financial data in a medical institution (see Japanese Patent Application Laid-Open No. 2005-004260, for example).

In the above information management system, however, various kinds of data are dispersion-managed in the subsystems of the respective departments, and are only associated with each other by a uniform code such as a patient ID. This has made it difficult to understand associations between elements forming the various kinds of data, resulting in difficulty in utilizing past data (medical empirical rules).

Further, while doctors study to accumulate knowledge themselves to deal with various patients, they have not always been able to effectively utilize past empirical rules beyond knowledge because human beings are not omnipotent and knowledge has its limits.

In addition, the technique disclosed in Japanese Patent Application Laid-Open No. 2005-004260 presents financial knowledge, not medical knowledge.

SUMMARY OF THE INVENTION

The present invention is directed to an information presentation system.

In an aspect of the invention, an information presentation system comprising: a first memory unit memorizing an associated information database storing associated information, the associated information being such that elements belonging to a plurality of element items respectively forming medical information on at least one patient are associated with each other between the plurality of element items; a condition-accepting unit accepting a selecting condition in response to user control, the selecting condition indicating one of an element belonging to one element item included in the plurality of element items, or a combination of elements belonging to a partial plurality of element items respectively included in the plurality of element items; a specifying unit specifying at least one output target item out of the plurality of element items in response to user control; and an output unit visibly outputting statistical information about the at least one output target item with respect to information satisfying the selecting condition out of the associated information.

Support information for medical treatment can be presented by effectively utilizing past medical empirical rules.

The present invention is also directed to a computer program controlling a computer to operate as an information presentation system.

The present invention is further directed to a computer software product including a recording medium on which a computer-readable software program is recorded.

Therefore, an object of the present invention is to provide a technique capable of presenting support information for medical treatment by effectively utilizing past medical empirical rules.

These and other objects, features, aspects and advantages of the present invention will become more apparent from the following detailed description of the present invention when taken in conjunction with the accompanying drawings.

BRIEF DESCRIPTION OF THE DRAWINGS

FIG. 6 illustrates the structuration of elements of numerous radiological reports.

FIG. 14 illustrates a display example of the medical-support-information presenting screen according to a modification.

FIG. 15 illustrates a condition-specifying screen according to a modification.

FIGS. 16 and 17 illustrate display examples of the medical-support-information presenting screen according to modifications.

DESCRIPTION OF THE PREFERRED EMBODIMENTS

Preferred embodiments of the present invention will be described with reference to the drawings.

<Configuration Outline of Medical-Information Presenting System>

Figure 1:
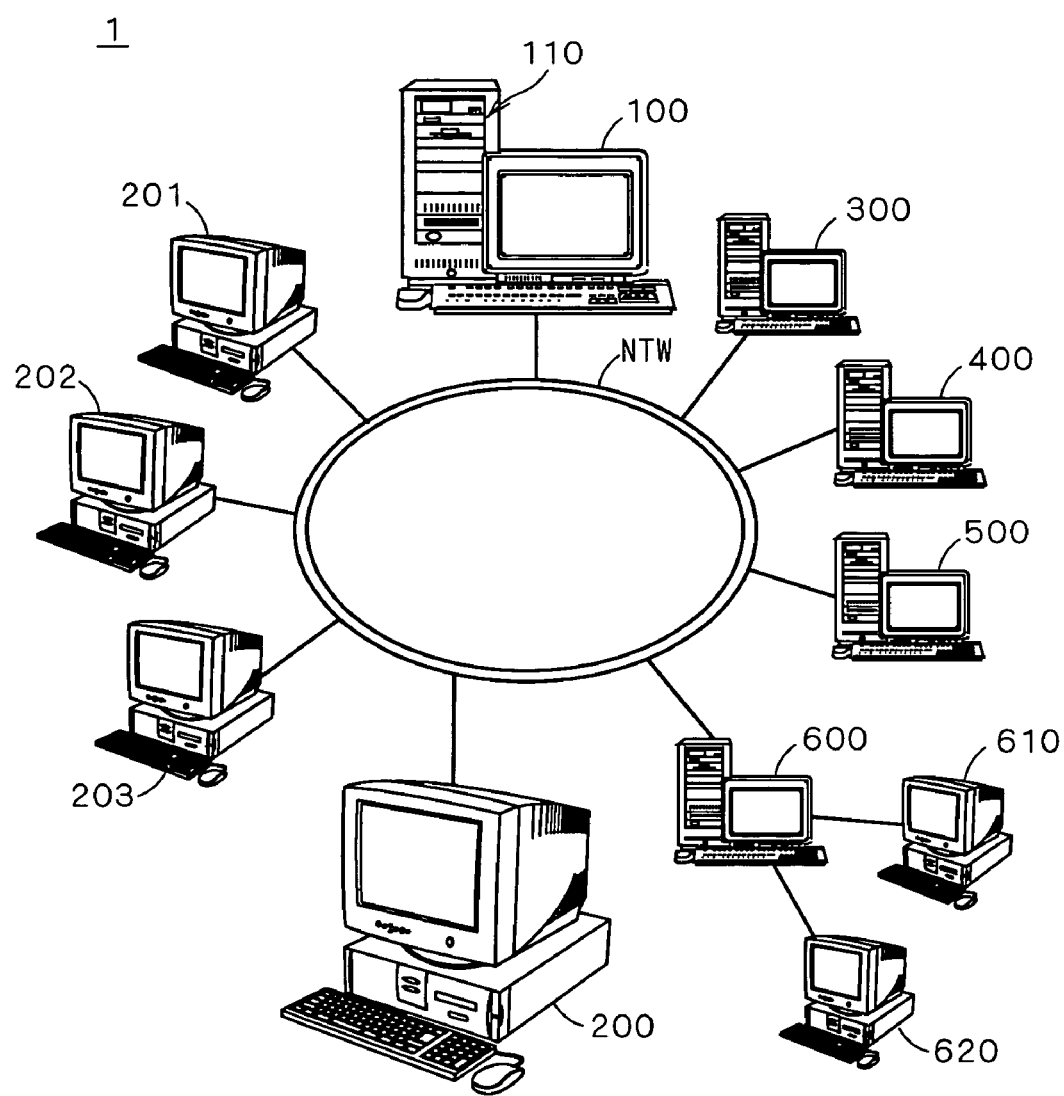
FIG. 1 shows a general configuration of a medical-information presenting system according to a preferred embodiment of the present invention.
Figure 2:
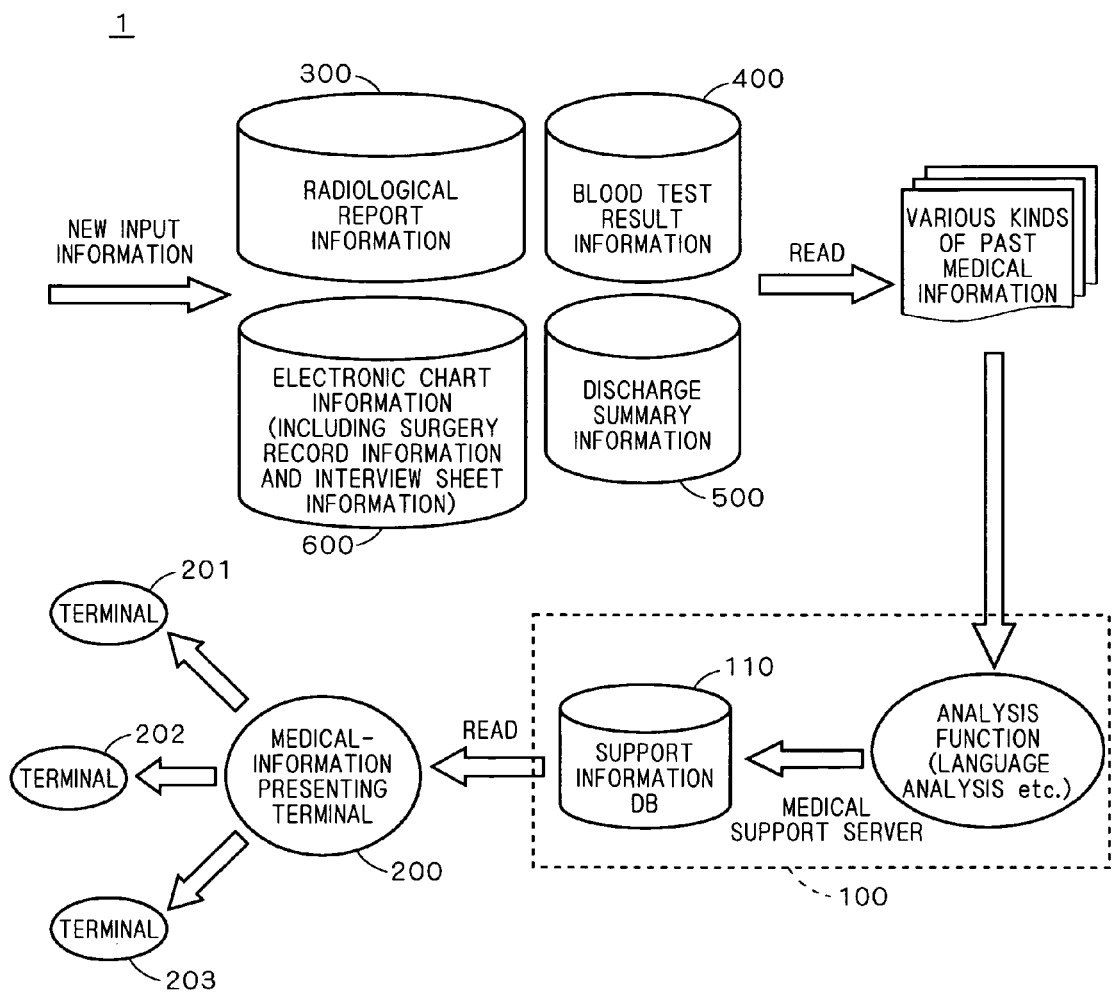
FIG. 2 shows a flow of information in the medical-information presenting system according to the preferred embodiment.

FIG. 1 shows a general configuration of a medical-information presenting system 1 according to a preferred embodiment of the present invention. FIG. 2 is a schematic diagram showing a flow of various kinds of information in the medical-information presenting system 1.

The medical-information presenting system 1 is a system for managing and processing medical information in a hospital, for example, and has a medical support server 100, a medical-information presenting terminal 200, predetermined communication equipment, such as terminals 201 to 203, a radiology information system (RIS) 300, a blood test information server 400, a discharge summary information server 500, and an electronic chart information server 600 connected through a network circuit NTW such as a LAN in a way that allows mutual data transmission and reception. The electronic chart information server 600 is connected to a surgery record information server 610 and an interview sheet information server 620 through a communications circuit.

The RIS 300 is installed in a radiology department in the hospital, for example, and stores various kinds of images of the results of radiation tests on numerous patients and information about radiological reports (radiological report information) in a manner that includes attribute information on the patients.

The blood test information server 400 is installed in a department that conducts a blood test in the hospital, for example, and stores information indicative of test results obtained by conducting blood tests on numerous patients (blood test result information) in a manner that includes attribute information on the patients.

The discharge summary information server 500 is installed in a department that prepares a discharge summary in the hospital, for example, and stores information indicative of discharge summaries prepared at the time of discharge from hospital on numerous patients (discharge summary information) in a manner that includes attribute information on the patients.

The surgery record information server 610 is installed in a department that manages surgery records in the hospital, for example, and stores information indicative of surgery records of numerous patients (surgery record information) in a manner that includes attribute information on the patients.

The interview sheet information server 620 is installed in a department that manages interview sheets in the hospital, for example, and stores information indicative of interview sheets of numerous patients (interview sheet information) in a manner that includes attribute information on the patients.

The electronic chart information server 600 is installed in a department that manages electronic charts in the hospital, for example, and obtains the surgery record information and the interview sheet information from the surgery record information server 610 and the interview sheet information server 620, respectively, to store medical records including those pieces of information, namely, information indicative of electronic charts of numerous patients (electronic chart information), in a manner that includes attribute information on the patients.

Medical-related information on patients including the blood test result information, the discharge summary information, the surgery record information, the interview sheet information, and the electronic chart information will henceforth be generally called "medical information".

The medical support server 100 is installed in a department that manages information collectively in the hospital, for example, and compiles numerous medical information on past patients to construct a database (support information DB) 110 memorizing information for supporting medical treatment, such as treatments and surgeries for patients (medical support information).

As illustrated in FIG. 2, the medical support server 100 obtains the various medical information from the RIS 300, the blood test information server 400, the discharge summary information server 500, and the electronic chart information server 600 through the network circuit NTW. The medical support server 100 then analyzes the various medical information by an analysis function such as language analysis to prepare the medical support information for supporting medical treatment, such as treatments and surgeries for patients, and stores the medical support information in the support information DB 110.

The medical-information presenting terminal 200 presents statistical information by utilizing the various medical support information stored in the support information DB 110. A statistical number such as a complete cure rate can be referred to on the medical-information presenting terminal 200 by selecting various kinds of conditions. Doctors, medical teams and patients are then able to take appropriate measures against symptoms with reference to the information presented on the medical-information presenting terminal 200.

Also, reference data can be sent in advance of a meeting and the like by distributing the information presented on the medical-information presenting terminal 200 to the terminals 201 to 203 and the like belonging to members of a medical team through the network circuit NTW.

The function of supporting medical treatment by presenting reference information for taking appropriate measures against the symptoms of a patient in the medical support server 100 may henceforth be called a "medical support function" (described later).

Each time a new patient or new symptom appears, the new information is input to the various medical information stored in the RIS 300, the blood test information server 400, the discharge summary information server 500, and the electronic chart information server 600. The new input information is reflected in order in the memory contents of the support information DB 110. Doctors, medical teams and patients are then always able to take appropriate measures against symptoms based on the latest medical information.

<Medical Support Function>

With the numerous medical information stored in the RIS 300, the blood test information server 400, the discharge summary information server 500, and the electronic chart information server 600 as the past knowledge, the medical support function includes a function of extracting necessary elements for presenting information for supporting medical treatment from the medical information and structuring the elements using the RDF (Resource Description Framework) and the like, to prepare and suitably present the medical support information.

The medical support function of the medical-information presenting system 1 will now be described.

Figure 3:
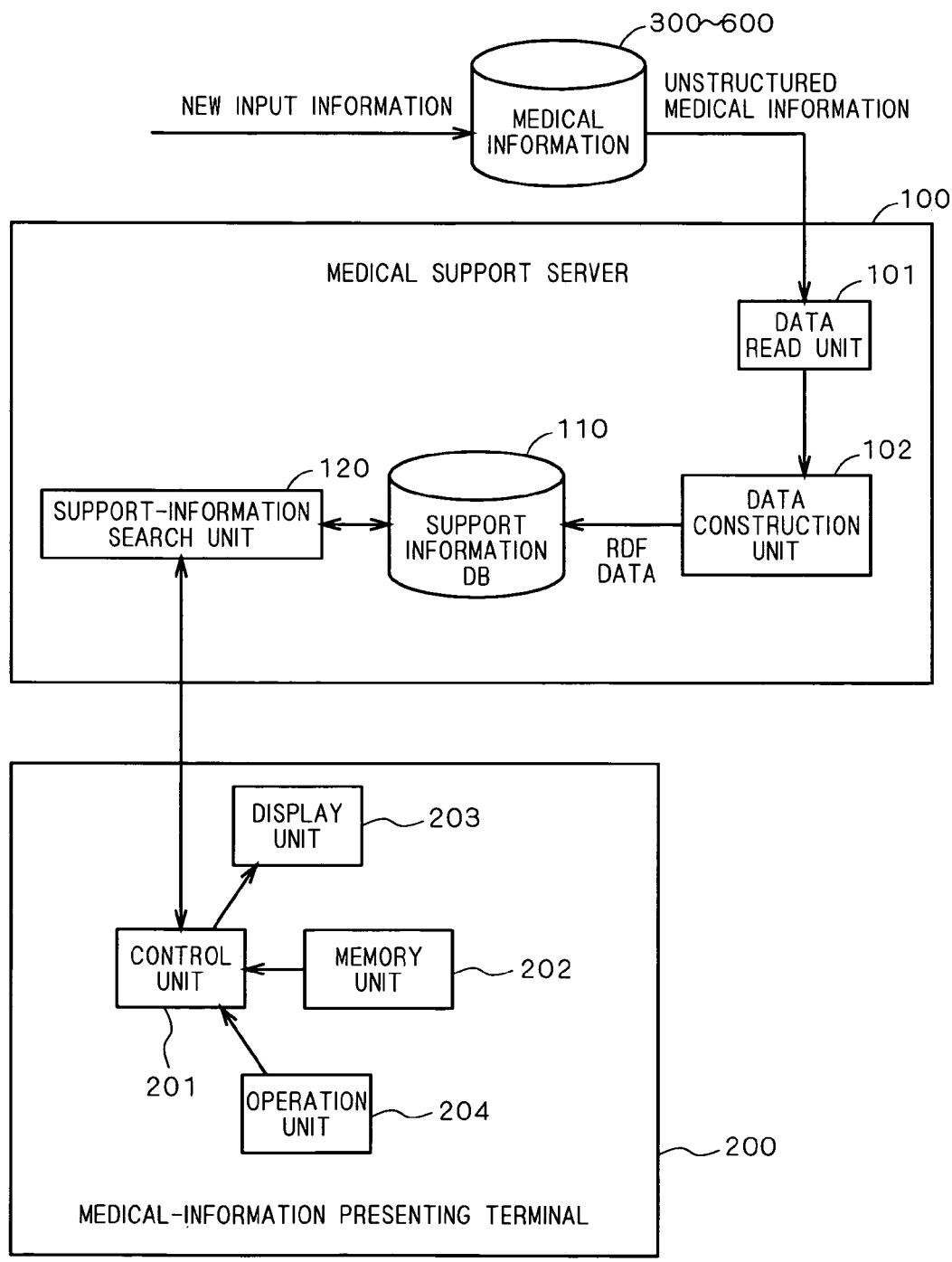
FIG. 3 is a block diagram illustrating a functional configuration regarding the generation of associated information and the presentation of medical support information.

FIG. 3 is a block diagram illustrating a functional configuration regarding the medical support function of the medical-information presenting system 1. The functional configuration shown in FIG. 3 is realized by executing a program memorized in a memory unit such as a hard disk by a CPU and the like in each of the medical support server 100 and the medical-information presenting terminal 200. Various kinds of data that are generated temporarily in the course of various kinds of information processing performed in this functional configuration are suitably memorized temporarily in a RAM and the like included in each of the medical support server 100 and the medical-information presenting terminal 200.

Operations realized by the medical support function mainly include predetermined information processing that includes: 1) an operation that prepares the medical support information (support-information preparing operation), and 2) an operation that presents various kinds of information for supporting medical treatment based on the medical support information (support-information presenting operation).

The support-information preparing operation and the support-information presenting operation will be described in order with reference to FIG. 3.

<Support-Information Preparing Operation>

A data read unit 101 reads the various kinds of medical information including the radiological report information, the blood test result information, the discharge summary information, and the electronic chart information (which includes the surgery record information and the interview sheet information) from the RIS 300, the blood test information server 400, the discharge summary information server 500, and the electronic chart information server 600, respectively, along with the attribute information on the patients. Then, the data read unit 101 sends the medical information to an information-generating unit, such as a data construction unit 102.

The data read unit 101 controls whether each piece of the medical information has been reflected in the medical support information, and reads pieces of the medical information that have not yet been reflected in the medical support information.

The data construction unit 102 extracts necessary elements from natural sentences and the attribute information included in the various kinds of medical information, for example, and structures the elements using the RDF. A language processing technique such as machine learning may be used to structure these elements forming the medical information.

Machine learning and the medical information structuration in the data construction unit 102 will now be described, taking the radiological report information included in the medical information as an example. A radiological report mainly includes sentences of findings described in natural sentence and attribute information on a patient.

The data construction unit 102 learns reference information for structuration by being supplied with a learning corpus as teaching data, for example.

The learning corpus includes large amounts of text data conforming to the format (text model) of sentences of the findings in the radiological report. This text model represents the structure of sentences of the findings in the radiological report, the structure listing photographing conditions, a region, basic findings (characteristics-conclusion), diagnosis 1 (characteristics-conclusion), and diagnosis 2 (characteristics-conclusion) in that order, for example. In the learning corpus, classified item names of elements forming the text model of sentences of the findings included in a model of the radiological report (also called a "report model") are tagged to words and phrases.

Examples of the element classified items include a "category of diagnosis (henceforth called a "category" for short), "photographing conditions", a "region", "basic findings", "general diagnosis (henceforth called "diagnosis 1" for short)", and "detailed diagnosis (henceforth called "diagnosis 2" for short)".

And in the learning corpus, for example, the element classified item name "category" is tagged to each of phrases such as "cerebral infarction", "ischemic change", and the like. The element classified item name "photographing conditions" is tagged to each of phrases such as "T1 image", "T2 image", and the like. The element classified item name "region" is tagged to each of phrases such as "frontal lobe", "temporal lobe", and the like. The element classified item name "basic findings" is tagged to each of phrases such as "punctate and ecchymotic high-signal area", "punctuate high-signal area", and the like. The element classified item name "diagnosis 1" is tagged to each of phrases such as "old cerebral infarction", "diffuse old cerebral infarction", and the like. The element classified item name "diagnosis 2" is tagged to each of phrases such as "thrombotic infarction", "embolic infarction", and the like.

The data construction unit 102 extracts words and phrases from the learning corpus, and memorizes them under their corresponding element classified items, respectively. Namely, the machine learning function of the data construction unit 102 learns and memorizes a word and/or phrase belonging to each element classified item under each element classified item, by using the teaching data including the learning corpus as learning materials and referring to the teaching data. At this time, variations of words, phrases and expressions are normalized to a degree.

The data construction unit 102 also learns and memorizes appearance patterns of the elements in the learning corpus. For example, the data construction unit 102 learns and memorizes an appearance pattern where the region "frontal lobe" is followed by a word or phrase belonging to the "basic findings", i.e. an appearance pattern indicative of what kinds of words or phrases belonging to what kinds of classified items appear in what order.

The data learned by and memorized in the data construction unit 102 is used as data of a model (model data) indicative of the types of element classified items into which elements forming existing radiological reports are decomposed.

Further, with the above-mentioned model data as the reference, an identification function of the data construction unit 102 identifies the element classified items and the actually used words or phrases in a radiological report that is input to the data construction unit 102.

Using the machine learning method described above, element classified items can be identified only for the elements (which are words and/or phrases in this case) given beforehand in the teaching data. The following machine learning method allows element classified items to be identified for elements not given beforehand in the teaching data as well.

For example, the machine learning function of the data construction unit 102 decomposes the learning corpus into morphemes through morphemic analysis, and learns an appearance pattern of a morpheme belonging to a certain classified item by using information and the like about the morpheme itself, the morpheme's part of speech, the morpheme's conjugation, and morphemes before and after that morpheme (two morphemes before and after that morpheme, for example), for each morpheme. The identification function of the data construction unit 102 is thus able to identify element classified items for elements (which are words and/or phrases in this case) not given beforehand as well in accordance with the pattern.

More specifically, when a phrase "along " (various words enter the "" part) appears frequently in the learning corpus, with words indicative of a region appearing frequently in the "" part, the machine learning function of the data construction unit 102 can learn a pattern where a word or phrase indicative of a region enters the "" part. Utilizing this pattern, the identification function of the data construction unit 102 can extract "hypophysis" as a word indicative of a region from a phrase "along/a/hypophysis" based on the context, in existing radiological reports. This machine learning can be realized by using the so-called SVM. This machine learning improves the accuracy of natural language processing.

Then, a data structuration function of the data construction unit 102 decomposes the various kinds of information included in the radiological report information into words and/or phrases (elements) under the element classified items and describes the elements in RDF based on the information identified by the identification function, thereby structuring the information about the radiological report. Since the appearance patterns of elements in existing radiological reports can also be identified at this time, information about those appearance patterns may be reflected in the model data used for the identification function to improve the model data. Namely, the more the existing radiological reports are analyzed, the more the model data can be improved. The data construction unit 102 then prepares structured data described in RDF that also includes attribute information about a request, a patient attribute, and a test attribute transmitted from the data read unit 101.

Figure 4:
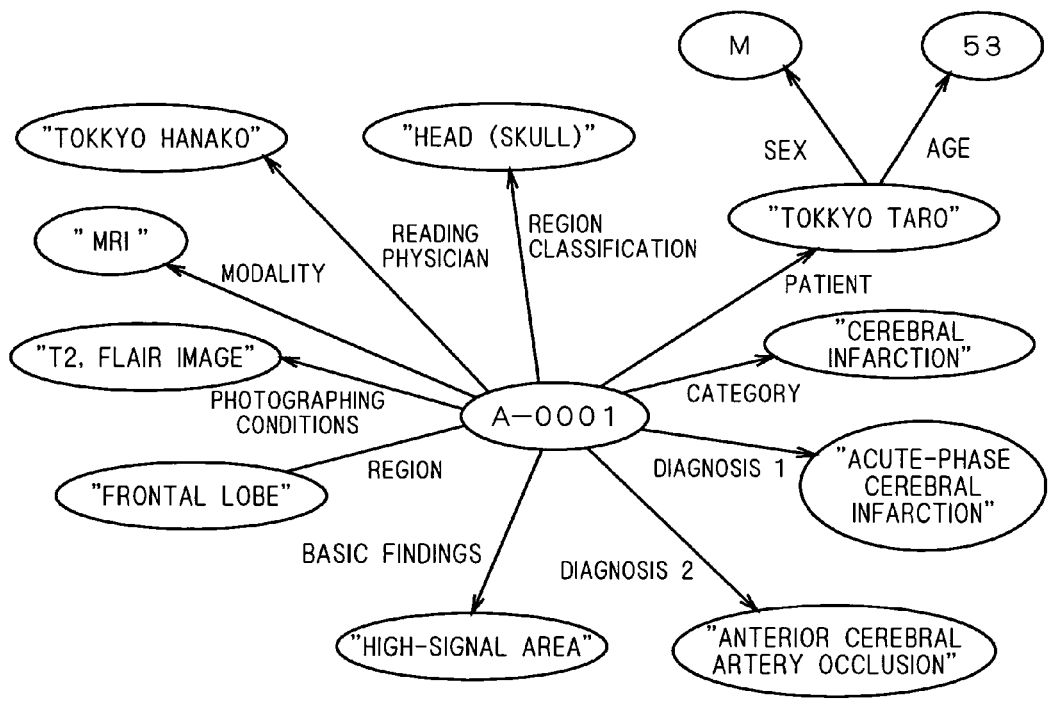
FIG. 4 illustrates the structuration of elements of a radiological report.

FIG. 4 illustrates data (henceforth also called "single-report structured data") obtained by structuring elements (which also include elements forming attribute information about an existing radiological report) of one radiological report.

As shown in FIG. 4, for a patient ID "A-0001", attribute values "cerebral infarction", "T2, FLAIR image", "frontal lobe", "high-signal area", "acute-phase cerebral infarction", and "anterior cerebral artery occlusion" are associated with the element classified items "category", "photographing conditions", "region", "basic findings", "diagnosis 1", and "diagnosis 2" as attribute items, respectively, and described in RDF. Also, "head (SKULL)", "Tokkyo Taro", "Tokkyo Hanako", and "MRI" are associated with attribute items "region classification", "patient", "reading physician", and "modality" about attribute information, respectively, and described in RDF. As to attributes of the patient, "M" and "53" are associated with attribute items "sex" and "age", respectively, and described in RDF. Attribute items for association in the single-report structured data are not limited to those illustrated in FIG. 4, but may include other attribute items included in information about test attributes, for example. Further, although FIG. 4 illustrates information about the head, information about a circulatory system or digestive system may be used, for example.

The data construction unit 102 prepares single-report structured data such as is shown in FIG. 4 for all pieces of the radiological report information stored in the RIS 300 by using the machine learning function, identification function, and data structuration function.

While the radiological report information included in the medical information has been described by way of example, the data construction unit 102 also performs the same language processing using machine learning and medical information structuration for the other pieces of information (blood test result information, discharge summary information, and electronic chart information) included in the medical information.

As a result, the data construction unit 102 prepares data in which the radiological report information, the blood test result information, the discharge summary information, and the electronic chart information about one case have been respectively structured (single-report structured data, single-blood-test-result structured data, single-discharge-summary structured data, and single-electronic-chart structured data). Such pieces of data are prepared for all cases. The single-report structured data, the single-blood-test-result structured data, the single-discharge-summary structured data, and the single-electronic-chart structured data may henceforth be generally called "structured data" suitably.

Figure 5:
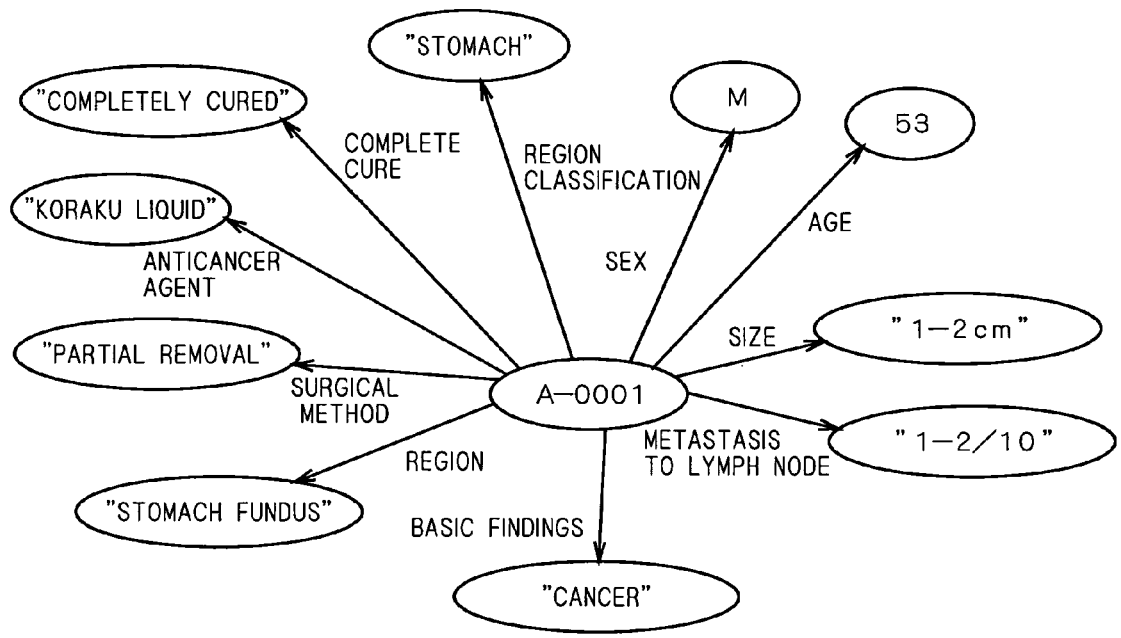
FIG. 5 illustrates the structuration of elements of a surgery record.

FIG. 5 illustrates an example of the single-electronic-chart structured data. Depicted in FIG. 5 is the surgery record information and, more specifically, the surgery record information about a digestive system by way of example.

In the single-electronic-chart structured data, as shown in FIG. 5, for a patient ID "A-0001", attribute values "stomach", "M", "cancer", "stomach fundus", "1-2 cm", "1-2/10", "partial removal", "Koraku liquid", and "completely cured" are associated with the element classified items "region classification", "sex", "basic findings", "region", "size" metastasis to lymph node" "surgical method", "anticancer agent", and "complete cure" as attribute items, respectively, and described in RDF. Attribute items for association in the single-electronic-chart structured data are not limited to those illustrated in FIG. 5, but may include other attribute items.

The data construction unit 102 performs the processing of arranging numerous attribute values under their corresponding attribute items, associating the values with each other and describing the values in RDF with respect to the single-report structured data, single-blood-test-result structured data, single-discharge-summary structured data, and single-electronic-chart structured data of one case, i.e. of the same patient ID, for all cases.

As a result of the processing, information (henceforth also called "network information") is prepared in which a plurality of attribute values (which are words and phrases in this case) are listed for each attribute item included in a plurality of attribute items, with the attribute values being associated like a network between the attribute items. The network information is memorized as the medical support information in a predetermined memory unit, to construct the support information DB 10.

Figure 7:
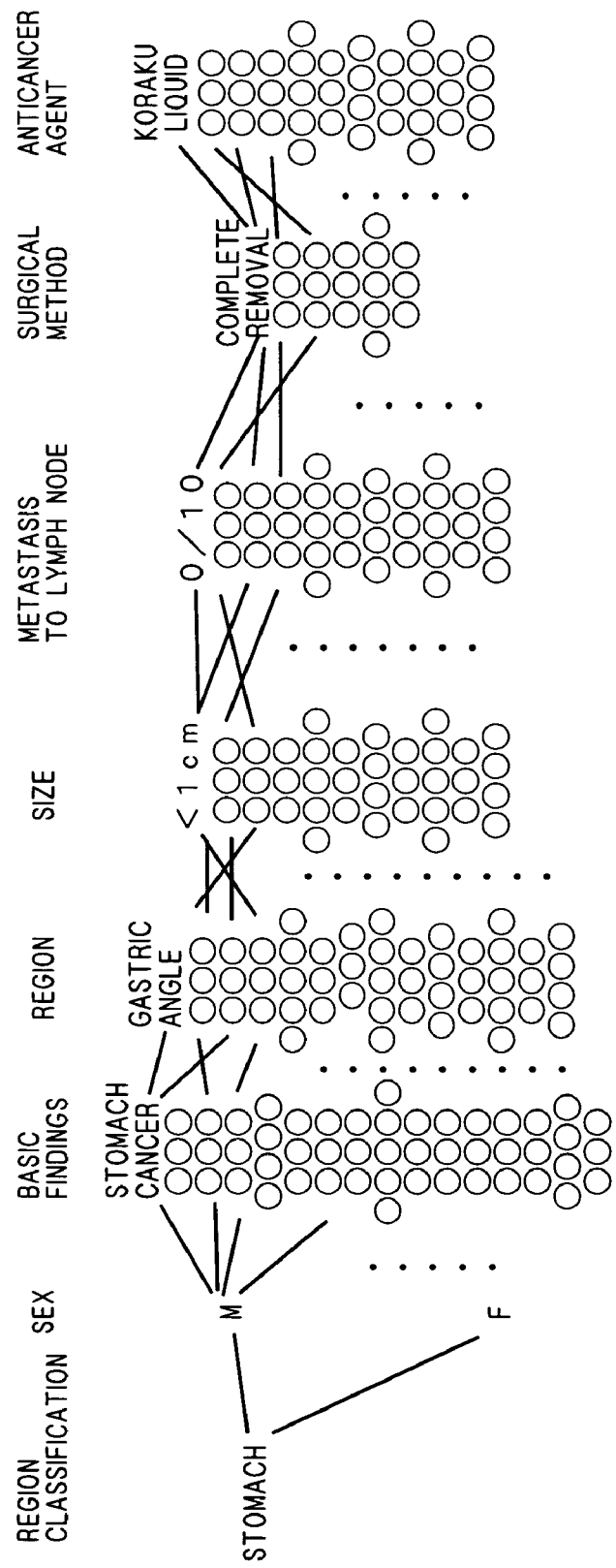
FIG. 7 illustrates the structuration of elements of numerous surgery records.

FIGS. 6 and 7 illustrate the structuration of elements of numerous existing medical information. For the sake of brevity, FIG. 6 illustrates part of the network information focusing on the items and elements of the radiological report, and FIG. 7 illustrates part of the network information focusing on the items and elements of the surgery record. Depicted in FIG. 6 is the network information about the region classification "head (SKULL)", and depicted in FIG. 7 is the network information about the region classification "stomach".

In FIGS. 6 and 7, associated words and phrases are illustrated as linked by lines. For brevity, words and phrases are suitably described as "○○○" and the like, and the lines indicative of associations are illustrated only in a relatively upper portion of the drawings while omitting the remaining lines.

When the network information is prepared in the data construction unit 102, the number of combinations of associated words and phrases between the items is counted for each case, to store the count information in the support information DB 110. For example, the number of combinations of words and phrases such as "head—MRI—M—cerebral infarction—T2, FLAIR image—frontal lobe—high-signal area—acute—phase cerebral infarction—anterior cerebral artery occlusion . . . " is memorized in the count information.

The network information stored in the support information DB 110 indicates the kinds of words and phrases described in existing medical information in a manner that associates the plurality of words and phrases with each other between the attribute items.

Therefore, if an item indicative of the condition and treatment of a patient, and an item indicative of whether the patient was completely cured after a predetermined period of time (e.g. five years), for example, are incorporated into the element items forming the medical information, and a combination of elements conforming to the actually encountered symptoms and treatment is selected by visibly outputting the network information, predictive results such as whether the patient will be completely cured will be effectively presented as a statistical value. It would be particularly effective if a template display mode were provided, with the attribute items as selective items (selective element items), and a plurality of words and phrases listed for each of the attribute items as selective choices (options).

Figure 8:
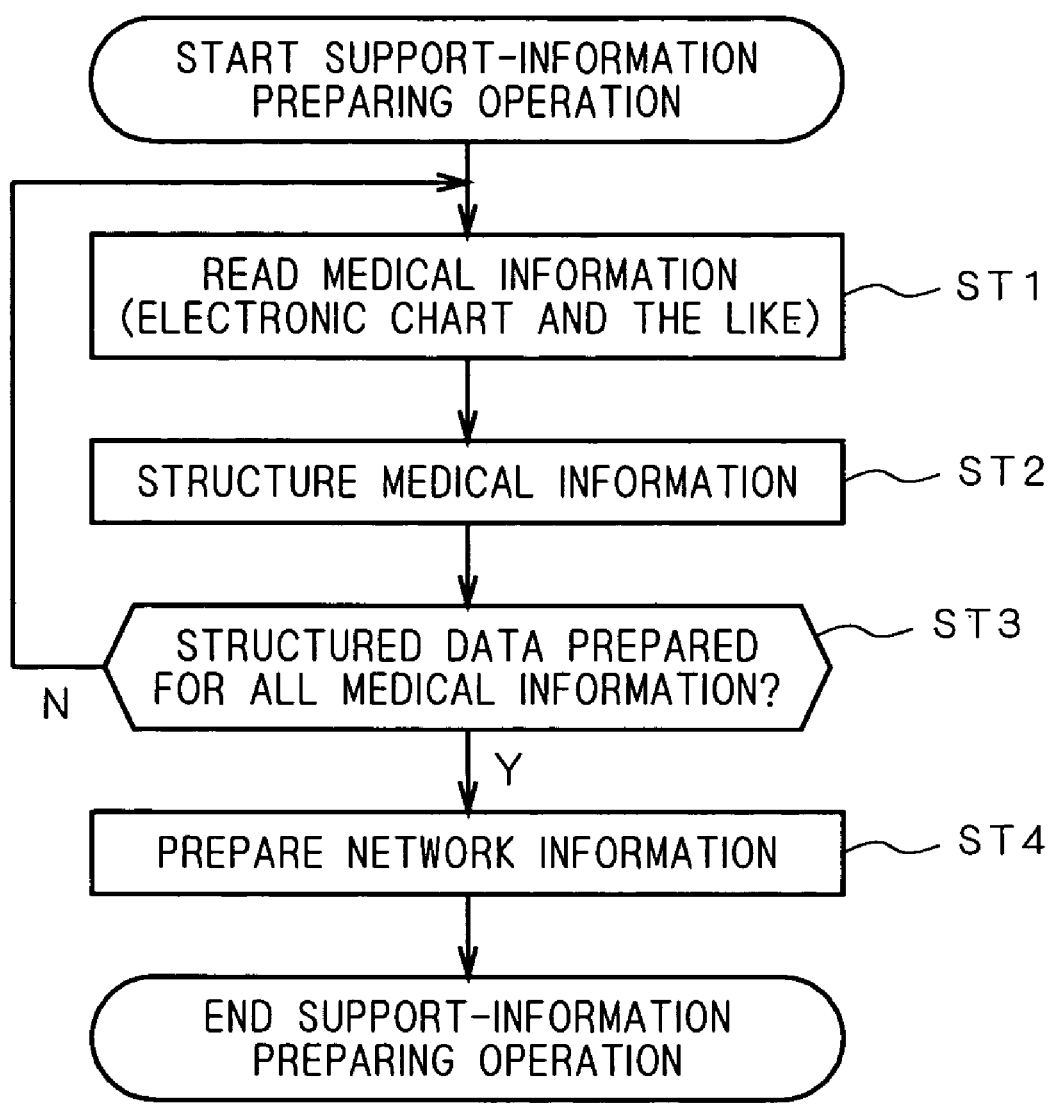
FIG. 8 is a flow chart illustrating an operation flow of a support-information preparing operation.

FIG. 8 is a flow chart illustrating an operation flow of the support-information preparing operation. This operation flow is realized by executing the program for realizing the medical support function in the medical support server 100.

In step ST1, the data read unit 101 reads one piece of medical information about one case from one of the following information-accepting/information-updating units: RIS 300, the blood test information server 400, the discharge summary information server 500, and the electronic chart information server 600. The medical information may be read preferentially in the order of the radiological report information, the blood test result information, the discharge summary information, and the electronic chart information (which includes the surgery record information and interview sheet information), for example.

In step ST2, the one piece of medical information read in step ST1 is structured by the functions of the data construction unit 102.

In step ST3, the data read unit 101 determines whether the structured data has been prepared for all pieces of the medical information stored in the RIS 300, the blood test information server 400, the discharge summary information server 500, and the electronic chart information server 600. When the structured data has not yet been prepared for all pieces of the medical information, processing returns to step ST1, where data and the like indicative of the next medical information is read to prepare structured data. Once the structured data has been prepared for all pieces of the medical information, processing continues to step ST4.

In step ST4, the network information is prepared based on the structured data for all pieces of the medical information, completing the operation flow. Information (associated information) including the network information and the count information is prepared then and stored in the support information DB 110.

The medical information accumulated in the RIS 300, the blood test information server 400, the discharge summary information server 500, and the electronic chart information server 600 increases with the addition of a case of a new patient. It would be effective if the medical information accumulated over time could also be used as the past knowledge. It would be particularly effective when an unprecedented case was newly accumulated, further improving the past knowledge. To that end, each time a new case (new input information) is added, the medical-information presenting system 1 performs the same processing as the operation shown in FIG. 8 on the new input information about the new case, and adds the new input information to the memory contents of the support information DB 110.

In this manner, the support information DB 110 stores consistent information on a case-by-case basis. When effectively displayed and utilized as a statistical numerical value, the information may be able to strongly support medical treatment.

Stomach cancer removal surgery will now be described by way of example.

Stomach cancer is typically detected through subjective symptoms, an examination with barium, an endoscopic examination and the like. In such cases, data exists such as an interview sheet and a radiological report. If stomach cancer is suspected, a close examination with an endoscope is performed as the next step, to prepare a radiological report.

Doctors determine a surgical method based on the examination results, and conduct stomach removal surgery. However, since it is difficult to identify a range of metastasis only by the close examination with an endoscope, an attempt is made to completely remove a range seen with metastasis while examining tissues sampled during the surgery under a microscope and the like. This surgery and the tissue examination results are recorded as a surgery record and tissue examination data.

When a cancerous cell has been completely removed, the patient is observed for a set period of time and discharged from hospital thereafter, with the preparation of a discharge summary. On the other hand, when it cannot be said with certainty that a cancerous cell has been completely removed, or when the cancerous cell has not been completely removed, the patient is observed while being administered with an anticancer agent. The patient is temporarily discharged from hospital with the preparation of a discharge summary in this case as well. If, unfortunately, the cancer recurs after the expiration of a set period of time, the patient is rehospitalized and undergoes surgery again if possible. When these developments are associated on a patient-by-patient basis by the data construction unit 102 and recorded in the support information DB 110 while being associated also with respect to similar data and cases, various kinds of analyses become possible.

For example, when cancer is detected in a lower part of the stomach that has metastasized to lymph nodes, it would be effective if the rate of recurrence after five years period could be referred to both in the case of complete stomach removal and in the case of only the lower part removal with administration of an anticancer agent. Stratification by age, stratification by sex, genetic information and the like, and stratification based on vital data such as blood test results will allow more effective analyses.

Next, the support-information presenting operation that presents various kinds of information for supporting medical treatment based on the medical support information will be described with specific examples.

<Support-Information Presenting Operation>

Figure 9:
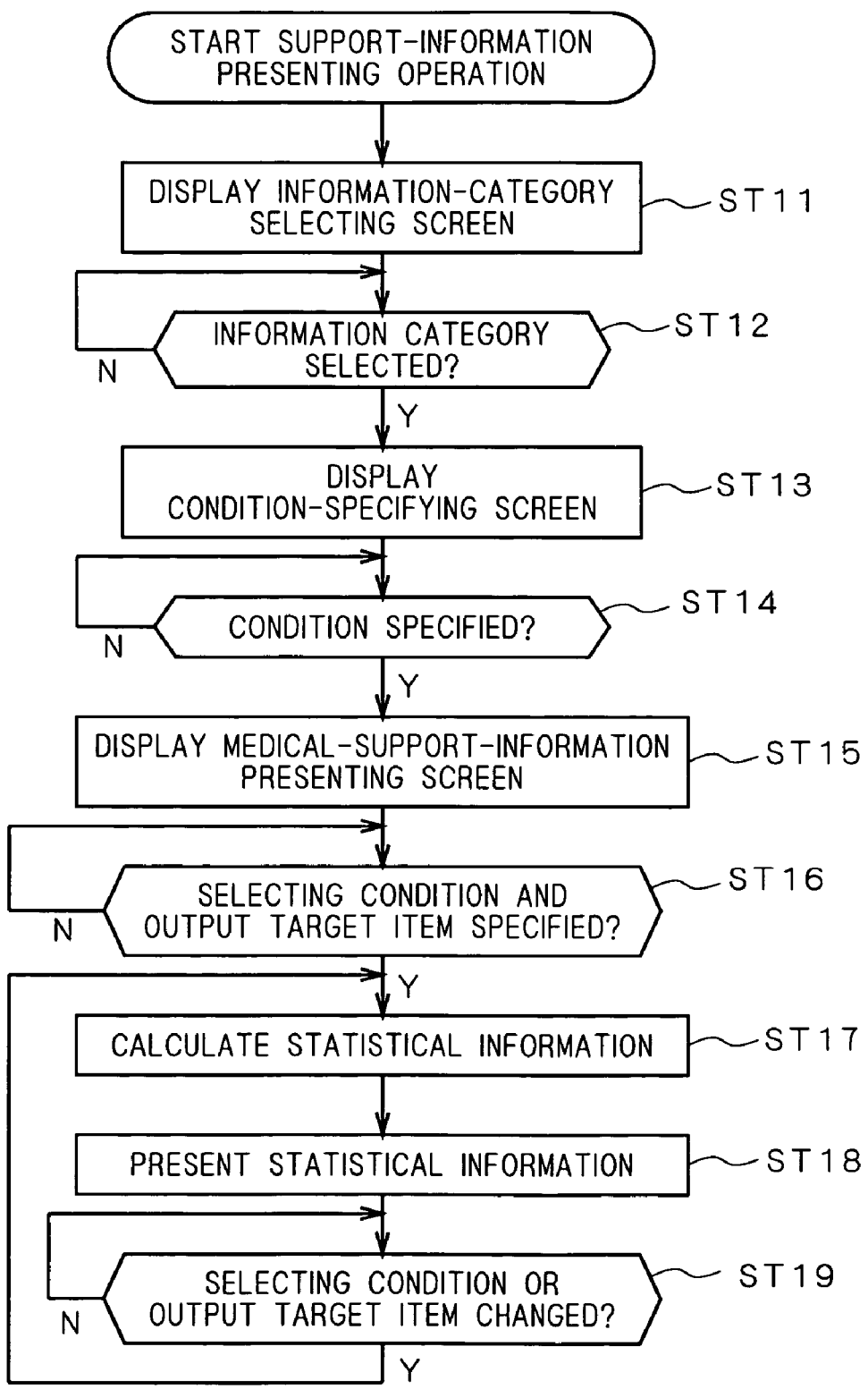
FIG. 9 is a flow chart illustrating an operation flow of a support-information presenting operation.

FIG. 9 is a flow chart illustrating an operation flow of the support-information presenting operation. This operation flow is realized by executing a program stored in an internal ROM and the like by a CPU and the like in each of the medical support server 100 and the medical-information presenting terminal 200. In the medical-information presenting terminal 200, for example, a specifying unit, such as control unit 201, executes a program (support-information presenting program) memorized in a memory unit 202.

First, a user such as a doctor appropriately operates an operation unit 204 including a keyboard, a mouse and the like at the medical-information presenting terminal 200, to instruct the execution of the support-information presenting program. The support-information presenting operation shown in FIG. 9 is thus started, and processing continues to step ST11.

In step ST11, an output unit, such as a display unit 203, displays a screen (information-category selecting screen) for selecting a category of information (information category) to which items belong, the items being about various kinds of conditions such as the condition and treatment of the patient including the symptoms.

Figure 10:
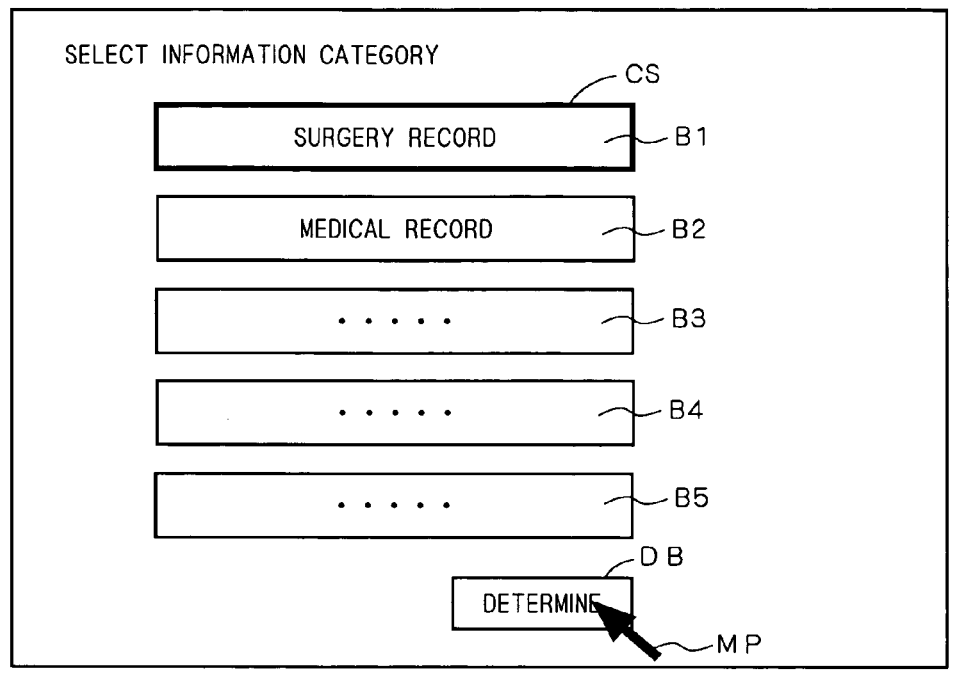
FIG. 10 illustrates an information-category selecting screen.

FIG. 10 illustrates a display example of an information-category selecting screen G1. The information-category selecting screen G1 displays a plurality of boxes B1 to B5 labeled with a category name of the medical information such as a "surgery record", a "medical record" and the like in order from the top in terms of space. The user such as a doctor appropriately operates the operation unit 204, to place a bold frame cursor CS at a box (e.g. a box B1) labeled with a desired category name out of the plurality of boxes B1 to B5, place a mouse pointer MP on a determination button DB, and left-click the mouse, thereby selecting the desired information category. Information of the selected information category is then supplied from the medical-information presenting terminal 200 to a condition-accepting unit, such as support-information search unit 120, in the medical support server 100. Note that support-information search unit 120 acts as an information-extracting unit.

In step ST12, it is determined whether an information category has been selected on the information-category selecting screen G1. The determination of step ST12 is repeated until an information category is selected. Once an information category has been selected, processing then continues to step ST13.

In step ST13, the display unit 203 displays a screen (condition-specifying screen) for specifying various kinds of conditions such as the condition and treatment of the patient including the symptoms. In this step, in response to the information of the information category having been selected and input to the support-information search unit 120 in step ST11 through step ST12, information about items of the network information (i.e. items forming the medical information) is transmitted from the support-information search unit 120 to the medical-information presenting terminal 200, to be reflected in the items listed on the condition-specifying screen displayed at the medical-information presenting terminal 200.

Figure 11:
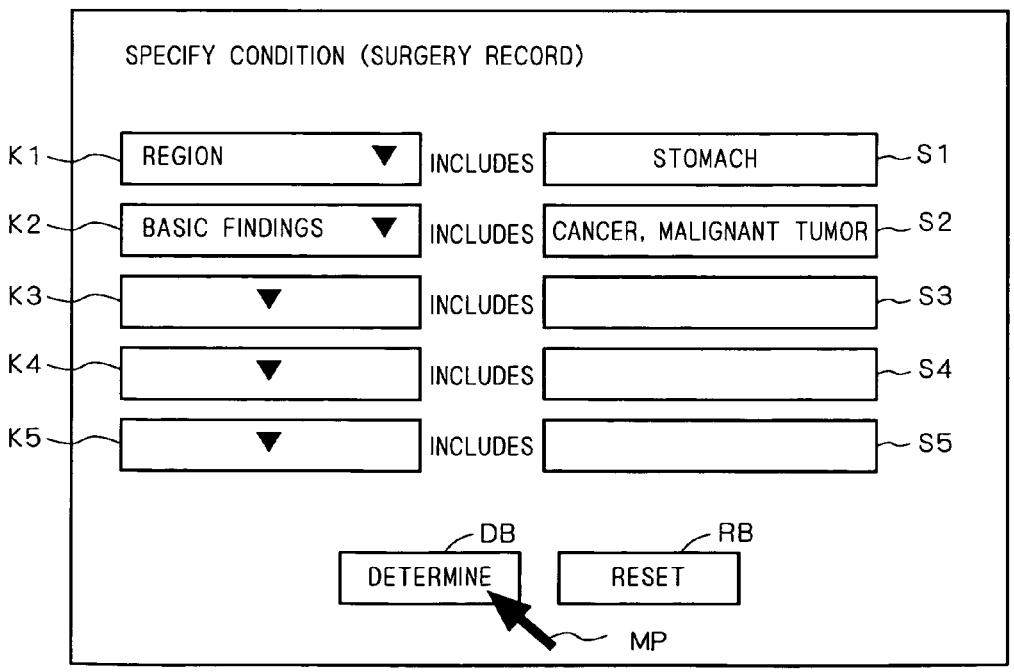
FIG. 11 illustrates a condition-specifying screen.

FIG. 11 illustrates a display example of a condition-specifying screen G2. The condition-specifying screen G2 displays five pull-down menu boxes K1 to K5 for specifying items of the network information stored in the support information DB 110 (i.e. items forming the medical information) in order from the top in terms of space on the left of the screen. In addition, input boxes S1 to S5 for inputting desired elements for the specified items are displayed correspondingly to the right of the menu boxes K1 to K5.

On the condition-specifying screen G2, the user such as a doctor appropriately operates the operation unit 204, to place the mouse pointer MP on a determination button DB and left-click the mouse with the menu boxes K1 to K5 displaying desired items and the input boxes S1 to S5 to the right displaying desired elements, thereby specifying a condition that specifies elements for the desired items.

The condition specified in this step is a condition (extracting condition) for extracting partial network information conforming to the condition out of the network information stored in the support information DB 110. Once the extracting condition has been specified, information indicative of the extracting condition is supplied from the medical-information presenting terminal 200 to the support-information search unit 120.

In FIG. 11, for example, a combination of items and elements where an item "region" includes an element "stomach", and an item "basic findings" includes an element "cancer, malignant tumor" is specified as the extracting condition.

In step ST14, it is determined whether an extracting condition has been specified on the condition-specifying screen G2. The determination of step ST14 is repeated until an extracting condition is specified. Once an extracting condition has been specified, processing then continues to step ST15.

In step ST15, a combination condition of elements is selected in accordance with the condition of the patient, and a desired item is specified as a target item (output target item) that outputs statistical information visibly. As a result, the display unit 203 displays a screen (medical-support-information presenting screen) that presents statistical information about the output target item.

In this step, the support-information search unit 120 searches the support information DB 110 in response to the specified extracting condition from the medical-information presenting terminal 200, and extracts partial network information corresponding to the extracting condition out of the entire network information. At this time, the support-information search unit 120 extracts the partial network information that satisfies the extracting condition out of the entire network information by referring to the count information stored in the support information DB 110. Partial count information corresponding to the extracted partial network information is also extracted. The partial network information and the partial count information thus extracted are temporarily memorized in the support information DB 110.

The partial network information and the partial count information will be generally called "partial associated information" suitably. The partial network information and the partial count information will suitably be called "network information" and "count information" for short, respectively. A template display (medical-support-information presenting screen) is then provided which is a visible view of the partial network information thus extracted.

Figure 12:
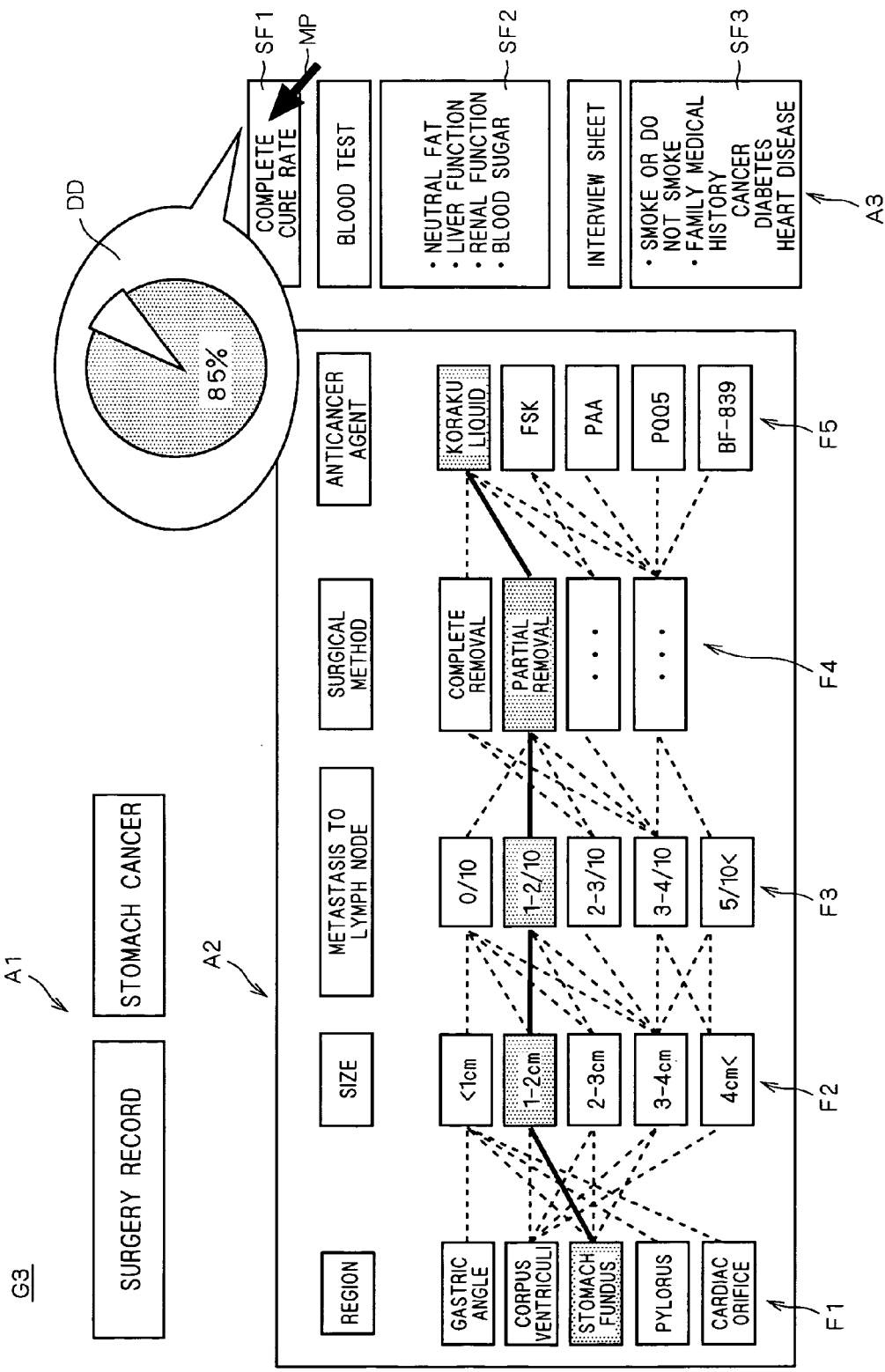
FIGS. 12 and 13 illustrate display examples of a medical-support-information presenting screen.

FIG. 12 illustrates a display example of a medical-support-information presenting screen G3.

The medical-support-information presenting screen G3 mainly includes an area (extracting-condition displaying area) A1 on the upper left of the screen, an area (items-and-elements displaying area) A2 in the center of the screen, and an area (statistical-information-presenting-item specifying area) A3 on the right of the screen.

The extracting-condition displaying area A1 displays the information category having been selected in step ST11 through step ST12, and the extracting condition having been specified in step ST13 through step ST14. In FIG. 12, the information category "surgery record" and the extracting condition "stomach cancer" are displayed.

The items-and-elements displaying area A2 displays items of the partial network information, namely, one or more items of the medical information that have been narrowed down, in order from the left. In FIG. 12, a plurality of elements F1 to F5 for the items "region", "size", "metastasis to lymph node", "surgical method", and "anticancer agent" are displayed, respectively, in order from the left.

More specifically, a plurality of elements (which are words and phrases "gastric angle" . . . "cardiac orifice" in this case) F1 are listed for the attribute item "region". A plurality of elements (which are numerical values "<1 cm" . . . "4 cm<" in this case) F2 are listed for the attribute item "size". A plurality of elements (which are values "0/10" . . . "5/10<" in this case) F3 are listed for the attribute item "metastasis to lymph node". A plurality of elements (which are words and phrases "complete removal" . . . " . . . " in this case) F4 are listed for the attribute item "surgical method". A plurality of elements (which are words "Koraku liquid" . . . "BF-839" in this case) F5 are listed for the attribute item "anticancer agent".

The five items displayed in the items-and-elements displaying area A2 are partial items included in the partial network information that has been extracted out of the entire network information in accordance with the extracting condition. A plurality of items to be displayed in the items-and-elements displaying area A2 are determined based on an information category and an extracting condition by the program executed in the medical support server 100. For the information category "surgery record" having been selected in step ST11 through step ST12, for example, one or more items not belonging to the items included in the extracting condition are displayed in the items-and-elements displaying area A2 in accordance with a predetermined rule.

Also in the items-and-elements displaying area A2, words and phrases associated with each other between the five items "region", "size", "metastasis to lymph node", "surgical method", and "anticancer agent" based on the partial network information extracted in accordance with the extracting condition are displayed as linked by display elements, such as lines (which are dashed lines in this case). In such ways, the number of options listed is limited to a degree in the template display which is a view of the partial network information out of the entire network information, which makes it easy to look at the options.

The user such as a doctor appropriately operates the operation unit 204 with the items-and-elements displaying area A2 displaying the partial network information, to place the mouse pointer MP on one element and left-click the mouse for each item, thereby specifying one element for each item. In FIG. 12, an element "stomach fundus" is specified for the item "region", an element "1-2 cm" for the item "size", an element "1-2/10" for the item "metastasis to lymph node", an element "partial removal" for the item "surgical method", and an element "Koraku liquid" for the item "anticancer agent". The specified elements are displayed distinguishably from the other elements (e.g. reverse display), and linked by display elements, such as solid lines. The solid lines linking the elements may be replaced by another display element (linking element) as long as being distinguishable from display elements indicative of the other associations.

As described above, in response to the operation by the user such as a doctor, an element belonging to each item is selected with respect to all items displayed in the items-and-elements displaying area A2 out of the plurality of items of the partial network information, thereby specifying a combination condition of elements (selecting condition). While the elements belonging to all items displayed in the items-and-elements displaying area A2 were selected above, elements (or a element) belonging to partial items (or one item) may be selected and specified as a selecting condition.

The statistical-information-presenting-item specifying area A3 lists one or more items (or items using a statistical expression of those items) not displayed in the items-and-elements displaying area A2 out of the plurality of items of the partial network information, in order from the top. Displayed in order from the top in FIG. 12 are an item "complete cure rate" SF1, four items "neutral fat", "liver function", "renal function", and "blood sugar" SF2 of the blood test result information, and four items "smoke or do not smoke", "family medical history (cancer)", "family medical history (diabetes)", and "family medical history (heart disease)" SF3 of the interview sheet information.

The statistical-information-presenting-item specifying area A3 is a menu display area listing items capable of outputting statistical information visibly. The mouse pointer MP is placed on one desired item out of the plurality of items listed in the area A3 and the mouse is left-clicked, thereby specifying a target item (output target item) that outputs statistical information visibly. In FIG. 12, the item "complete cure rate" SF1 is specified as the output target item.

In step ST16, it is determined whether a combination condition of elements (selecting condition) and an item (output target item) that outputs statistical information visibly have been specified on the medical-support-information presenting screen G3. The determination of step ST16 is repeated until a selecting condition and an output target item are specified. Once they have been specified, processing then continues to step ST17.

The selecting condition and the output target item having been specified in step ST15 through step ST16 are then output from the medical-information presenting terminal 200, to be accepted by the support-information search unit 120.

In step ST17, the support-information search unit 120 calculates statistical information about the output target item, with respect to the information that satisfies the selecting condition out of the partial network information stored in the support information DB 110.

For example, statistical information indicative of a "complete cure rate" is calculated as follows. As described above, with respect to the information about cases that satisfy the selecting condition out of the partial network information, namely, element combination information, the number of element combinations in which an element "completely cured" is associated with an item "complete cure", and the number of element combinations in which an element "not completely cured" is associated with the item "complete cure" are obtained from the partial count information, thereby calculating the statistical information indicative of a "complete cure rate".

In step ST18, the statistical information having been calculated by the support-information search unit 120 in step ST17 is visibly presented (displayed) on the medical-support-information presenting screen G3. In FIG. 12, a pie graph DD indicative of the complete cure rate is displayed.

The user such as a doctor is able to learn by looking at the medical-support-information presenting screen G3 shown in FIG. 12 that a complete cure rate (i.e. a complete cure ratio) after five years period is 85%, on conditions that "there exists stomach cancer the size from 1 to 2 cm on the stomach fundus, that metastases to lymph nodes are detected at one or two spots of ten sampling spots, that partial removal surgery was conducted, and that the Koraku liquid was administered as an anticancer agent thereafter".

By specifying a combination of the condition of the patient's symptoms, surgical method, treatment and the like based on examination results and the like as described above, a complete cure rate for development prediction can be learned. This allows surgery and a plan of treatment to be determined appropriately.

The statistical information can also be used effectively as a scientific material to persuade the other members of a medical team. For example, in order to effectively utilize examination information and treatment, and statistical information indicative of development prediction corresponding to a combination of the examination information and the treatment, the medical-support-information presenting screen G3 may be provided with a button instructing transmission to registered members. With a left-click of the mouse with the mouse pointer MP on the button, examination information and treatment, and statistical information indicative of development prediction corresponding to a combination thereof may be distributed from the medical-information presenting terminal 200 to the terminals 201 to 203 belonging to previously registered members.

More specifically, the members may be registered with a predetermined mailing list beforehand by using the e-mail function of the medical-information presenting terminal 200. Upon transmission instruction to the registered members, information can be added to e-mail and distributed to the terminals 201 to 203 which are communication equipment used by the members.

With this configuration, scientific information about a conference for determining surgery and a plan of treatment can be presented to the members of a medical team prior to the conference, for example. This distribution operation may be executed automatically when predetermined conditions are satisfied, such as when the selecting condition or output target item has not been changed for a predetermined period of time.

The statistical information presented on the medical-support-information presenting screen G3 can also be utilized effectively as a persuasive material in giving an explanation to the patient.

In step ST19, it is determined whether the specified selecting condition or output target item has been changed in response to the operation of the operation unit 204 by the user such as a doctor on the medical-support-information presenting screen G3. The determination of step ST19 is repeated until the specified selecting condition or output target item is changed. Once the specified selecting condition or output target item has been changed, processing then returns to step ST17. Then, statistical information is calculated about an output target item under the new selecting condition (step ST17), and the statistical information is displayed on the medical-support-information presenting screen G3 (step ST18), for example.

Figure 13:
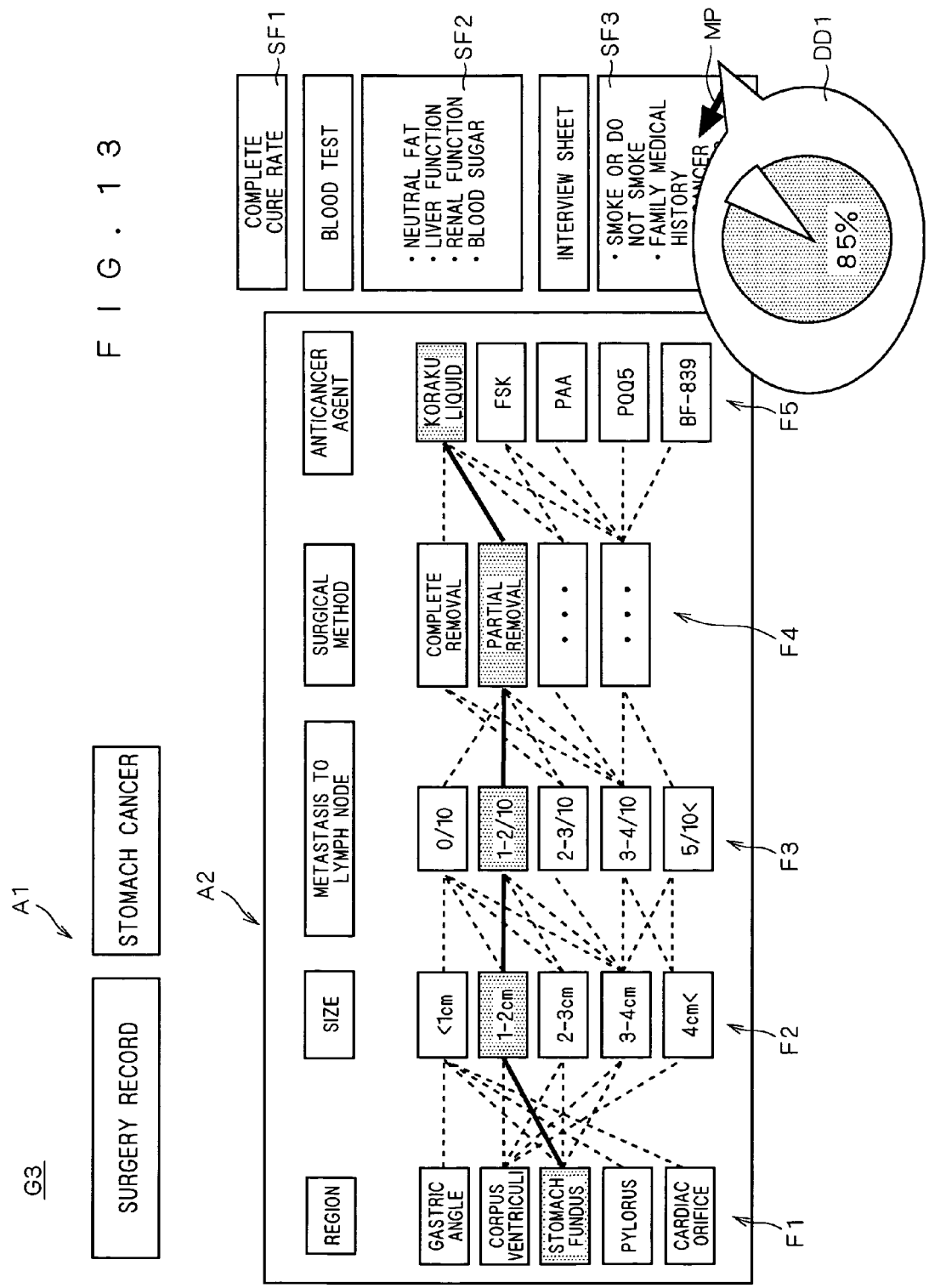

FIG. 13 illustrates a display example of the medical-support-information presenting screen G3 when the item "family medical history (cancer)" is specified as the output target item under the same selecting condition as in FIG. 12. In this case, with respect to information about cases that satisfy the selecting condition out of the partial network information, namely, element combination information, the number of element combinations in which an element "YES" is associated with the item "family medical history (cancer)", and the number of element combinations in which an element "NO" is associated with the item "family medical history (cancer)" are obtained from the partial count information, thereby calculating statistical information indicative of a rate (i.e. a ratio) of "family medical history (cancer)". In FIG. 13, a pie graph DD1 indicative of the rate of "family medical history (cancer)" is displayed.

The user such as a doctor is able to learn by looking at the medical-support-information presenting screen G3 shown in FIG. 13 that a rate of cancer in the family is 85%, on conditions that "there exists stomach cancer the size from 1 to 2 cm on the stomach fundus, that metastases to lymph nodes are detected at one or two spots of ten sampling spots, that partial removal surgery was conducted, and that the Koraku liquid was administered as an anticancer agent thereafter".

As has been described, the medical-information presenting system 1 according to the preferred embodiment of the present invention prepares and stores information (associated information) in the support information DB 110, the information being such that elements belonging to a plurality of element items respectively forming medical information on at least one patient are associated with each other between the items. Then, on the medical-support-information presenting screen G3 displayed at the display unit 203, a selecting condition selecting one or more elements and an output target item are specified and input in response to the operation by the user such as a doctor. As a result, with respect to information that satisfies the selecting condition out of the associated information, statistical information about the output target item is visibly output at the display unit 203. Therefore, past medical empirical rules can be effectively utilized to present support information for medical treatment.

Further, information indicative of element association between the items is added based on the medical information about a case of a new patient, thus updating the network information stored in the support information DB 110. Therefore, the knowledge changed over time can be effectively utilized to present support information for medical treatment. The network information may be updated each time new medical information is added, or in a predetermined cycle. When the network information is updated, the materials having been distributed to the members of the medical team attending the conference may be modified to reflect the latest network information and redistributed.

Further, the medical-support-information presenting screen G3 displays a view, the view being such that elements belonging to a plurality of element items respectively forming medical information on at least one patient are associated with each other between the items. Accordingly, the user such as a doctor can specify a selecting condition easily by referring to the displayed view. Particularly in this embodiment where the partial network information corresponding to the extracting condition specified by the user such as a doctor is extracted to display a view of the partial network information, the user can specify a selecting condition further easily on the displayed view of network information that has been narrowed down to a degree and easy to look at.

Additionally, the network information can be described easily in RDF.

Moreover, predetermined information processing including language processing is performed on the plurality pieces of medical information stored in the RIS 300, the blood test information server 400, the discharge summary information server 500, and the electronic chart information server 600, thereby generating the network information in which elements belonging to items respectively are associated with each other between the items. Therefore, the medical information accumulated in the past can be effectively utilized to present support information for medical treatment.

<Modifications>

The preferred embodiment described above is not intended to limit the scope of the present invention.

For example, while a combination of elements about the items of the surgery record information was specified as the selecting condition in the preferred embodiment, a combination of elements about items of various kinds of information may be specified as a selecting condition.

Described below are variations in selecting an information category on the information-category selecting screen G1, variations in specifying an extracting condition on the condition-specifying screen G2, and variations in displaying a view, and specifying a selecting condition and an output target item on the medical-support-information presenting screen G3.

<(1) When Statistical Information About Tumor Marker is Presented>

Utilizing the support information DB 10, a threshold value between a normal value and an abnormal value can be statistically obtained particularly about vital data and the like including blood test results, and the statistical information can be presented for use in making a diagnosis.

FIG. 14 illustrates a medical-support-information presenting screen G13 presenting statistical information about vital data.

The medical-support-information presenting screen G13 corresponds to the medical-support-information presenting screen G3 in the above preferred embodiment, and mainly includes an area (extracting-condition displaying area) A11 on the upper left of the screen, an area (items-and-elements displaying area) A12 on the right of the screen, and an area (statistical-information-presenting-item specifying area) A13 on the left of the screen. The extracting-condition displaying area A11, the items-and-elements displaying area A12, and the statistical-information-presenting-item specifying area A13 correspond to the extracting-condition displaying area A1, the items-and-elements displaying area A2, and the statistical-information-presenting-item specifying area A3, respectively, but display information of different contents due to different conditions from the above preferred embodiment.

The contents of information displayed on the medical-support-information presenting screen G13 will be described.

The extracting-condition displaying area A11 displays an information category having been selected on the information-category selecting screen G1, and an extracting condition having been specified on the condition-specifying screen G2. In FIG. 14, an information category "blood test result" and an extracting condition "stomach cancer" are displayed.

The items-and-elements displaying area A12 displays items of partial network information, namely, one or more items of the medical information that have been narrowed down, in order from the left. In FIG. 14, a plurality of elements F1 to F3 for items "region", "size", and "metastasis to lymph node" are displayed, respectively, in order from the left. The same elements as the elements F1 to F3 in FIG. 12 are listed for the plurality of elements F1 to F3 in FIG. 14.

The three items displayed in the items-and-elements displaying area A12 are partial items included in the partial network information that has been extracted out of the entire network information in accordance with the extracting condition. A plurality of items to be displayed in the items-and-elements displaying area A12 are determined based on an information category and an extracting condition by the program executed in the medical support server 100.

The user such as a doctor appropriately operates the operation unit 204 with the items-and-elements displaying area A12 displaying the partial network information, to place the mouse pointer MP on one element and left-click the mouse for each item, thereby specifying one element for each item.

In FIG. 14, an element "stomach fundus" is specified for the item "region", an element "1-2 cm" for the item "size", and an element "1-2/10" for the item "metastasis to lymph node". The specified elements are displayed distinguishably from the other elements (e.g. reverse display), and linked by solid lines.

The statistical-information-presenting-item specifying area A13 displays items "lipid", "carbohydrate metabolism", "liver function", "renal function", "inflammation", "anaemia", "tumor marker (CEA)", "tumor marker (AFP)", and "tumor marker (CA-19-9)", in order from the top.

The mouse pointer MP is placed on one desired item out of the plurality of items listed in the statistical-information-presenting-item specifying area A13, and the mouse is left-clicked, thereby specifying a target item (output target item) that outputs statistical information visibly. In FIG. 14, the item "tumor marker (CEA)" is specified as the output target item.

When the item "tumor marker (CEA)" is specified as the output target item, with respect to the information about cases that satisfy the selecting condition out of the partial network information, namely, element combination information, an element belonging to the item "tumor marker (CEA)", which is a numerical value, is referred to calculate the relationship between the numerical value and the frequency of occurrence about the item "tumor marker (CEA)". In FIG. 14, the calculated relationship between the numerical value and the frequency of occurrence about the item "tumor marker (CEA)" is visibly presented (displayed) in a distribution diagram DD2, with the horizontal axis indicating the numerical value and the vertical axis indicating the frequency. The distribution diagram DD2 shows the statistical information corresponding to the cases that satisfy the selecting condition and, for comparison purposes, the relationship between the numerical value and the frequency of occurrence about the item "tumor marker (CEA)" when stomach cancer was not particularly recognized.

By referring to the distribution diagram DD2, the user such as a doctor is able to specifically predict the current condition of the patient using the statistical numerical value information about the item "tumor marker (CEA)" and the like.

<(2) When Interview Sheet and Genetic Incidence are Utilized>

As described above, the support information DB 110 memorizes information about items forming the interview sheet information and the elements belonging to the items.

An interview sheet typically describes a family medical history. Incorporating this information into the support information DB 110, the patient can be subjected to further various analyses and treatments. Preventive treatment and the like become possible particularly for conditions with highly hereditary factors such as high blood pressure and diabetes by specifying a selecting condition appropriately and referring to statistical information.

A specific example will be described of presenting statistical information by utilizing interview sheet information.

FIG. 15 illustrates a display example of a condition-specifying screen G22. The condition-specifying screen G22 displays information of different contents from the condition-specifying screen G2 in the above preferred embodiment. The contents of display will thus be mainly described.

The condition-specifying screen G22 displays five pull-down menu boxes K21 to K25 for specifying items of the network information stored in the support information DB 110 (items forming a medical record in this case) in order from the top in terms of space on the left of the screen. In addition, input boxes S21 to S25 for inputting desired elements for the specified items are displayed correspondingly to the right of the menu boxes K21 to K25.

On the condition-specifying screen G22, the user such as a doctor appropriately operates the operation unit 204, to place the mouse pointer MP on a determination button DB2 and left-click the mouse with the menu boxes K21 to K25 displaying desired items and the input boxes S21 to S25 to the right displaying desired elements, thereby specifying a condition that specifies elements for the desired items.

The condition specified in this step is a condition (extracting condition) for extracting partial network information conforming to the condition out of the network information stored in the support information DB 110. Once the extracting condition has been specified, information indicative of the extracting condition is supplied from the medical-information presenting terminal 200 to the support-information search unit 120.

In FIG. 15, for example, a combination of items and elements where an item "interview sheet" includes an element "cancer in the family", and an item "diagnosis record" includes an element "stomach cancer" is specified as the extracting condition.

FIG. 16 illustrates a medical-support-information presenting screen G23, which is displayed under the extracting condition shown in FIG. 15.

The medical-support-information presenting screen G23 corresponds to the medical-support-information presenting screen G3 in the above preferred embodiment, and has the extracting-condition displaying area A1, the items-and-elements displaying area A2, and the statistical-information-presenting-item specifying area A3 arranged in the same fashion. Yet the medical-support-information presenting screen G23 displays information of different contents due to different conditions from the above preferred embodiment.

The contents of information displayed on the medical-support-information presenting screen G23 will be described.

The extracting-condition displaying area A1 displays the extracting condition that "medical record includes stomach cancer", and "interview sheet includes cancer in the family".

The items-and-elements displaying area A2 displays items of partial network information, namely, one or more items of the medical information that have been narrowed down, in order from the left. In FIG. 16, a plurality of elements F21 to F25 for items "interview sheet", "region", "size", and "metastasis to lymph node" are displayed, respectively, in order from the left. The plurality of elements F21 indicative of the relationship with the subject, and the plurality of elements F22 indicative of a medical history are displayed for the item "interview sheet". More specifically, elements indicative of the relationship with the subject "father", "mother", "grandfather", "grandmother", and "brother" are listed for the plurality of elements F21, and elements indicative of a medical history "stomach cancer", "liver cancer", "colorectal cancer", "esophagus cancer", and "breast cancer" are listed for the plurality of elements F22. The same elements as the plurality of elements F1 to F3 in FIG. 12 are listed for the plurality of elements F23 to F25.

The user such as a doctor appropriately operates the operation unit 204 with the items-and-elements displaying area A2 displaying the partial network information, to place the mouse pointer MP on one element belonging to each of the five element groups of the plurality of elements F21 to F25 and left-click the mouse respectively, thereby specifying one element for each item.

In FIG. 16, elements "father" and "stomach cancer" are specified for the item "interview sheet", an element "stomach fundus" for the item "region", an element "1-2 cm" for the item "size", and an element "1-2/10" for the item "metastasis to lymph node". The specified elements are displayed distinguishably from the other elements (e.g. reverse display), and linked by solid lines.

The statistical-information-presenting-item specifying area A3 displays an item "complete cure rate" SF21, and nine items of the blood test result information "lipid", "carbohydrate metabolism", "liver function", "renal function", "inflammation", "anaemia", "tumor marker (CEA)", "tumor marker (AFP)", and "tumor marker (CA-19-9) SF22, in order from the top.

The mouse pointer MP is placed on one desired item out of the plurality of items listed in the statistical-information-presenting-item specifying area A3, and the mouse is left-clicked, thereby specifying a target item (output target item) that outputs statistical information visibly. In FIG. 16, the item "complete cure rate" SF21 is specified as the output target item, and a pie graph DD3 indicative of the complete cure rate is displayed.

The user is able to learn by looking at the medical-support-information presenting screen G23 shown in FIG. 16 that a complete cure rate after five years period is 85%, on conditions that "the father had stomach cancer, that there exists stomach cancer the size from 1 to 2 cm on the stomach fundus, and that metastases to lymph nodes are detected at one or two spots of ten sampling spots".

By specifying a combination of conditions including the condition of the patient based on an interview sheet and the like as described above, a complete cure rate for development prediction can be learned. This allows surgery and a plan of treatment to be determined appropriately. If there is a difference in complete cure rate depending on whether a father had stomach cancer, for example, treatment can be employed on the basis of genetic information.

When the item "tumor marker (CEA)" is specified as the output target item on the medical-support-information presenting screen G23 as shown in FIG. 17, for example, with respect to the information about cases that satisfy the selecting condition out of the partial network information, namely, element combination information, an element belonging to the item "tumor marker (CEA)", which is a numerical value, is referred to calculate the relationship between the numerical value and the frequency of occurrence about the item "tumor marker (CEA)". In FIG. 17, the calculated relationship between the numerical value and the frequency of occurrence about the item "tumor marker (CEA)" is visibly presented (displayed) in a distribution diagram DD4, with the horizontal axis indicating the numerical value and the vertical axis indicating the frequency. Like the distribution diagram DD2 shown in FIG. 14, the distribution diagram DD4 shows the statistical information corresponding to the cases that satisfy the selecting condition and, for comparison purposes, the relationship between the numerical value and the frequency of occurrence about the item "tumor marker (CEA)" when stomach cancer was not particularly recognized.

By referring to the distribution diagram DD4, the user is able to specifically predict the current condition of the patient using the current numerical value of the "tumor marker (CEA)" of the patient and the statistical numerical value information.

In the future, direct genetic information such as examination results of genetic information using DNA and the like may be incorporated into the medical information to improve the information stored in the support information DB 110, so that the relationship between genetic information and a case can be referred to quantitatively by specifying a selecting condition appropriately. This allows appropriate treatment and measures to be employed based on further scientific evidence.

<(3) When Interview Sheet and Genetic Incidence are Utilized when Patient is Rehospitalized>

Generally speaking, a complete cure rate for a case is lower when the patient is hospitalized the second time around than when the patient is hospitalized initially. Described below is the case when an element of information indicative of rehospitalization belongs to a diagnosis record included in the medical information stored in the support information DB 110.

Figure 18:
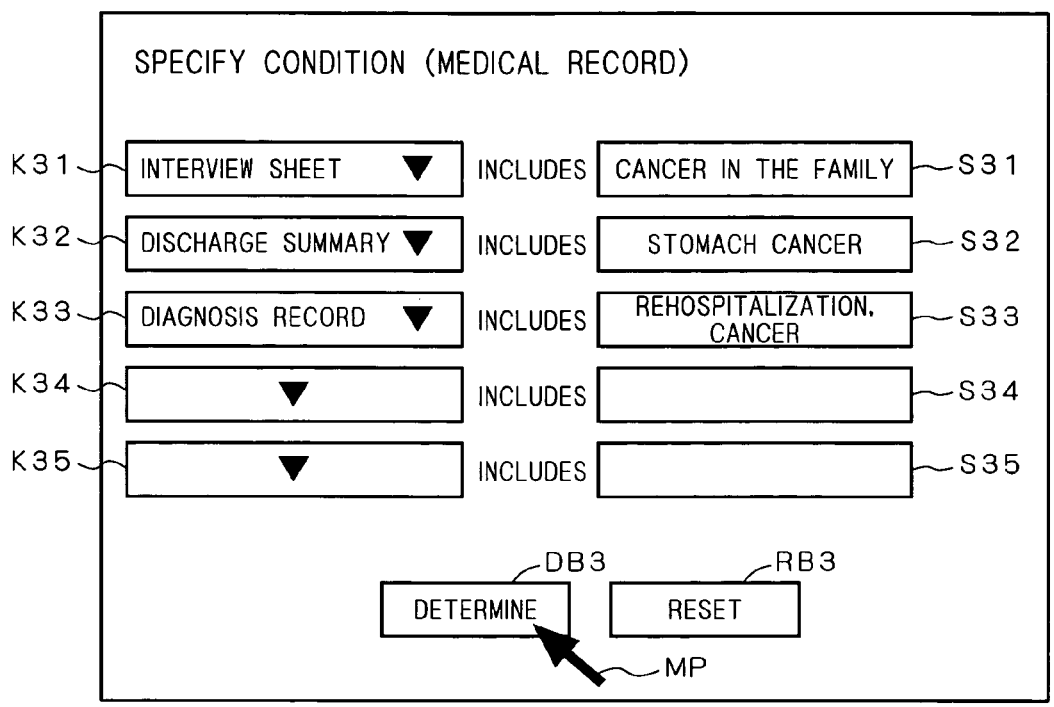
FIG. 18 illustrates a condition-specifying screen according to a modification.

FIG. 18 illustrates a display example of a condition-specifying screen G32. The condition-specifying screen G32 displays information of different contents from the condition-specifying screen G2 in the above preferred embodiment. The contents of display will thus be mainly described.

The condition-specifying screen G32 displays five pull-down menu boxes K31 to K35 for specifying items of the network information stored in the support information DB 110 (items forming a medical record in this case) in order from the top in terms of space on the left of the screen. In addition, input boxes S31 to S35 for inputting desired elements for the specified items are displayed correspondingly to the right of the menu boxes K31 to K35.

On the condition-specifying screen G32, the user such as a doctor appropriately operates the operation unit 204, to place the mouse pointer MP on a determination button DB3 and left-click the mouse with the menu boxes K31 to K35 displaying desired items and the input boxes S31 to S35 to the right displaying desired elements, thereby specifying a condition that specifies elements for the desired items.

The condition specified in this step is a condition (extracting condition) for extracting partial network information conforming to the condition out of the network information stored in the support information DB 110. Once the extracting condition has been specified, information indicative of the extracting condition is supplied from the medical-information presenting terminal 200 to the support-information search unit 120.

In FIG. 18, for example, a combination of items and elements where an item "interview sheet" includes an element "cancer in the family", an item "discharge summary" includes an element "stomach cancer", and an item "diagnosis record" includes two elements "rehospitalization, cancer" is specified as the extracting condition.

Figure 19:
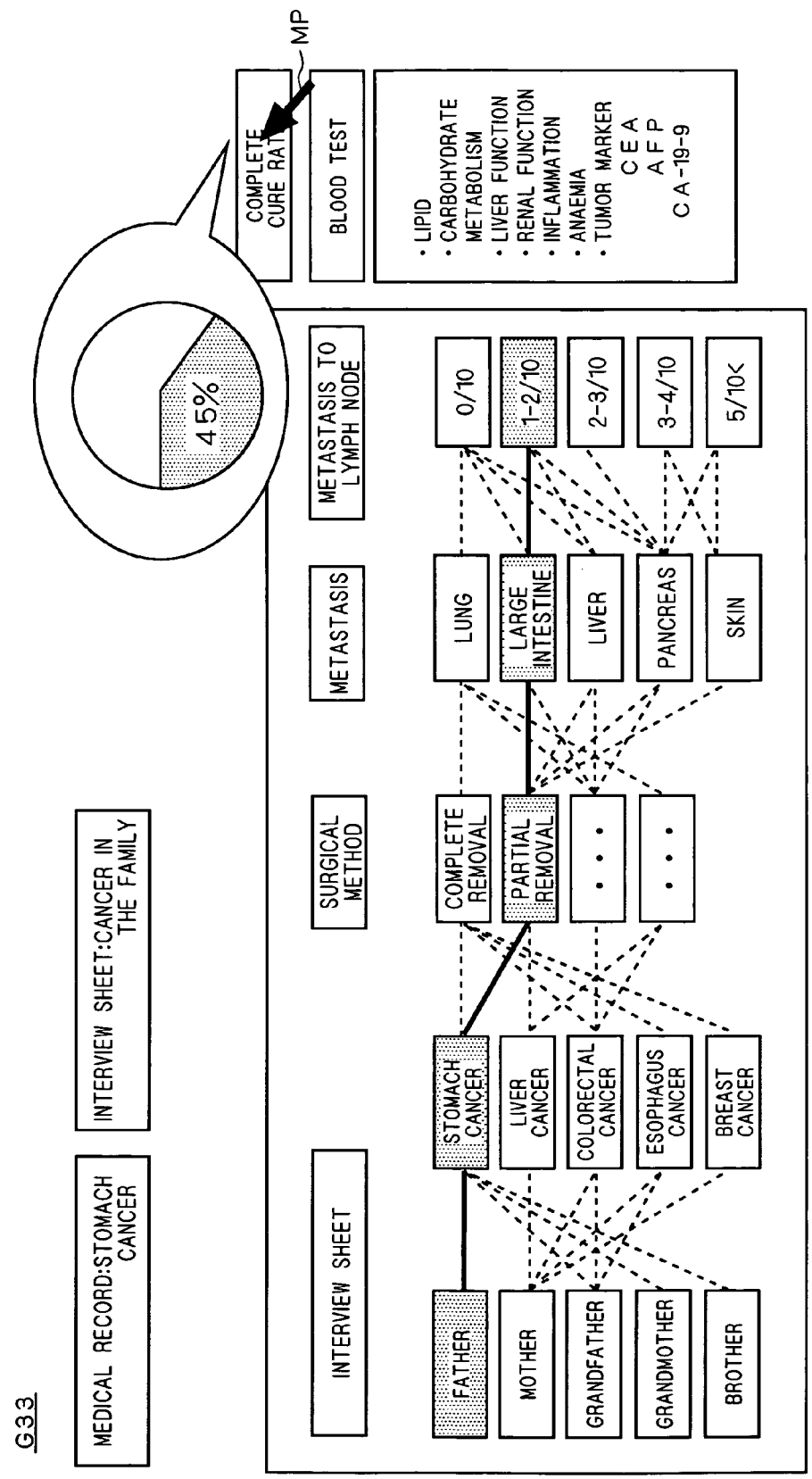
FIGS. 19 and 20 illustrate display examples of the medical-support-information presenting screen according to modifications.

FIG. 19 illustrates a medical-support-information presenting screen G33, which is displayed under the extracting condition shown in FIG. 18.

Figure 20:
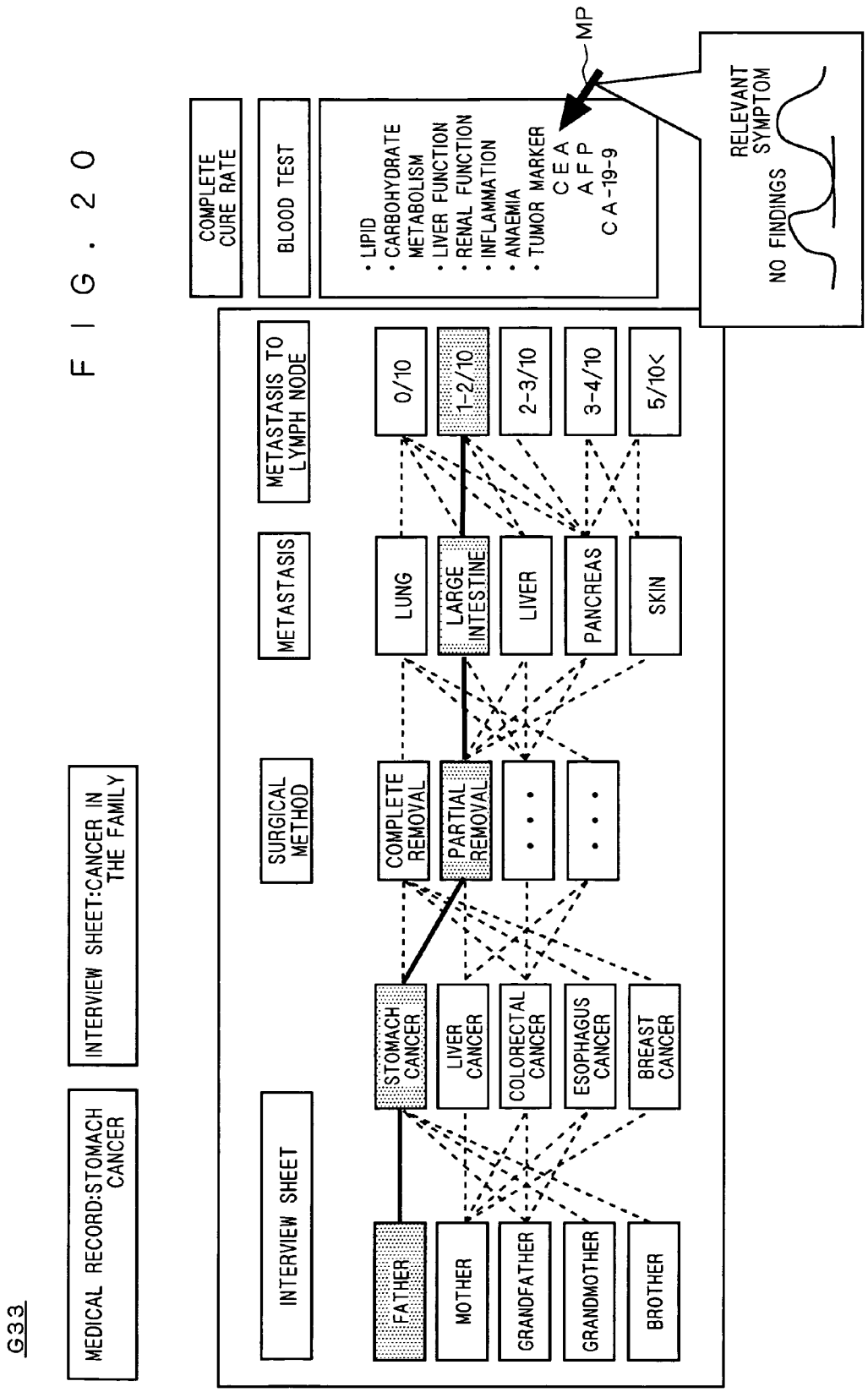

The medical-support-information presenting screen G33 shown in FIG. 19, which further includes the element "rehospitalization" belonging to the item "diagnosis record" in the extracting condition, visibly presents statistical information indicative of a reduced complete cure rate from 85% to 45% as compared with the medical-support-information presenting screen G23 shown in FIG. 16 under the same selecting condition. Likewise, the medical-support-information presenting screen G33 shown in FIG. 20, which further includes the element "rehospitalization" in the extracting condition, presents an altered distribution diagram for the item "tumor marker (CEA)" as compared with the medical-support-information presenting screen G23 shown in FIG. 17 under the same selecting condition.

In such ways, with the addition of information about rehospitalization to the medical information, more reference information can be presented for analyzing the patient's symptoms, or determining surgery and a plan of treatment.

In the above preferred embodiment, the medical information on a patient includes a family medical history. Alternatively, information indicative of a medical history of at least one of the subject and the family may be included. Consequently, support information for medical treatment (e.g. possibility of onset) can be presented in consideration of genetic incidence including information on the subject in a conference and the like.

In the above preferred embodiment, the medical information on a patient includes the blood test result information, the discharge summary information, the surgery record information, the interview sheet information, and the electronic chart information. Alternatively, one or more pieces of information may be included that includes attribute information on a patient who developed symptoms of any case, examination information on a patient who developed the symptoms, examination information on a patient who has not developed the symptoms, information indicative of treatment, and information indicative of a recovery degree. Consequently, support information for medical treatment can be presented by effectively utilizing various kinds of past medical empirical rules.

The examination information may suitably include various kinds of images like ones obtained from X-ray photography, various kinds of reports typified by a radiological report, and examination results of a biopsy typified by a blood test.

In the above preferred embodiment, the user such as a doctor specifies a selecting condition and refers to the resultantly presented statistical information, to determine surgery and a plan of treatment, or employ the statistical information for a conference. Alternatively, a selecting condition corresponding to the symptoms of a patient may suitably be specified to present statistical information in front of the patient, to use the statistical information as a reference material for informed consent where the patient is asked to consent to surgery and a plan of treatment.

An example of utilizing the support information DB 110 for informed consent will be described.

Taking stomach cancer as an example, removal surgery while leaving the upper part of a stomach accelerates postoperative recovery because a digestive function is preserved, but leaves a fear of side effects from an anticancer agent and a risk of recurrence. By specifying a selecting condition appropriately on those particulars during informed consent, a rate of occurrence of side effects from the anticancer agent and a rate of recurrence of patients having the same case can be presented to the patient statistically and quantitatively. The patient is then able to make judgments easily about surgery and a plan of treatment with such presentation of statistical and quantitative information.

Further, by incorporating at least one or more items including items "symptom development", "treatment period", and "cost" into the items that may be specified as the output target item, and specifying elements of a surgical method and treatment for such items as "surgical method" and "anticancer agent" as a selecting condition, statistical information can be presented that shows symptom development, treatment period, and cost required for surgery and treatment of patients having the same case. Accordingly, useful information for informed consent can be presented easily.

Still further, by incorporating items "side effects" and "correlation between cost and course" into the items that may be specified as the output target item, informed consent can proceed with reference to information such as a risk of side effects and the cost of surgery and treatment course.

As for breast cancer, complete cure rates with breast removal and with a combination of administration of an anticancer agent and radiation treatment can be presented to a patient by specifying an information category and a selecting condition appropriately. Consequently, the patient can select and consent to treatment based on statistical data stratified by focus position, size, age, genetic information, vital data and the like.

Additionally, the plurality of element items forming the medical information on at least one patient may include an item about at least one of symptom development and a change in condition of the patient. For example, the medical information may include information to the effect that the patient was hospitalized after coming down with cerebral infarction, but the patient's condition took a sudden turn for the worse with a ruptured blood vessel, and the patient died after developing cerebral hemorrhage. Consequently, support information for medical treatment can be presented by effectively utilizing past medical empirical rules even when the condition of a patient has taken a sudden turn for the worse.

In the above preferred embodiment, the selecting condition and output target item are specified to calculate statistical information about the output target item on the medical-support-information presenting screen G3. Alternatively, statistical information about a predetermined item such as a complete cure rate, which is expected to present statistical information with a high frequency among the plurality of element items forming the medical information, may be calculated beforehand for all selecting conditions or a predetermined number of selecting conditions specified with a high frequency, and included in the associated information in the support information DB 110. Consequently, statistical information can be presented more quickly about the predetermined item.

In the above preferred embodiment, the statistical information is presented as a pie graph indicative of a ratio (rate), and a graph indicative of numerical value distribution. Alternatively, the statistical information may be displayed as a graph plotting numerical value dispersion, for example. Namely, statistical information should be visibly presented in the form of at least one of ratio, distribution and dispersion. Consequently, statistical and easy-to-understand information can be presented to the user, resulting in the same effects as the above preferred embodiment.

In the above preferred embodiment, the view of the network information is displayed for specifying a selecting condition on the medical-support-information presenting screen G3. Alternatively, an element belonging to each item of the plurality of items included in the network information may be selected in order in such a way that the selection of an element belonging to one item allows the selection of an item belonging to the next item. Nevertheless, the view of the network information makes it easier to select the respective elements belonging to the items with a higher degree of usability.

In the above preferred embodiment, a plurality of words (which include phrases) as a plurality of elements belonging to the items respectively are associated with each other between the items and stored in the support information DB 110. Alternatively, when the medical information such as a report includes elements other than words such as diagrams and images, elements other than words such as a plurality of diagrams and images may be included in the plurality of elements belonging to the items respectively.

With respect to the item "region", for example, a plurality of diagrams indicative of a region corresponding to the plurality of elements may be employed instead of words as the plurality of elements. For example, three region phrases "left frontal lobe", "right frontal lobe", and "bilateral frontal lobe" of a brain may be represented by diagrams shown in FIGS. 21A to 21C. The use of such diagrams instead of a plurality of words allows a region to be selected easily by intuition.

Figure 21A:
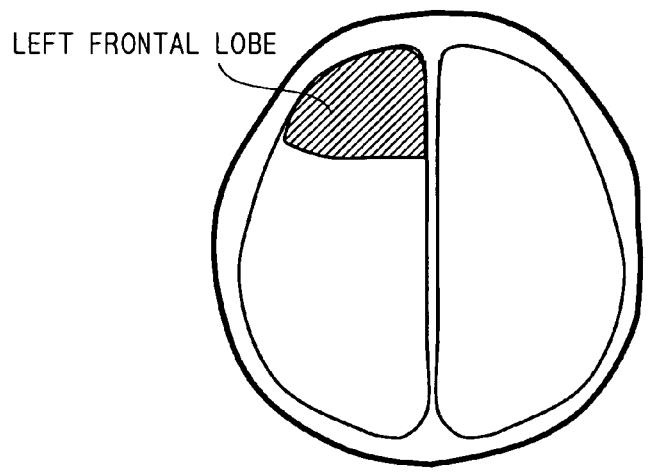
FIGS. 21A to 21C and FIGS. 22A to 22C illustrate display elements according to modifications.
Figure 21B:
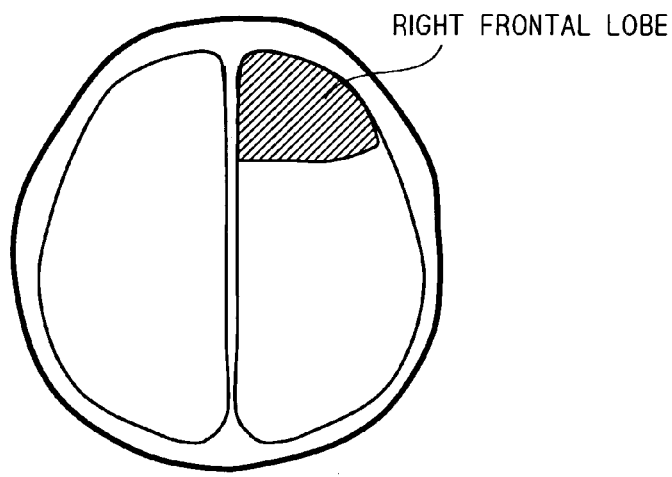
Figure 21C:
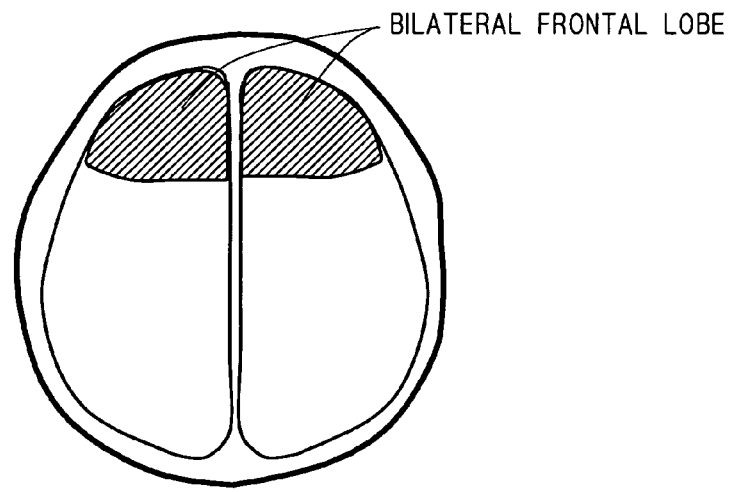

Instead of the diagrams shown in FIGS. 21A to 21C, a general view of a brain may be displayed that is divided into detailed regions such as "left frontal lobe" and "right frontal lobe", for a detailed region to be specified by a mouse pointer and the like on the view.

Diagrams, images and the like indicative of a region are not limited to those shown in FIGS. 21A to 21C, but may include those indicative of various regions, such as diagrams indicative of parts of the lungs.

Figure 22A:
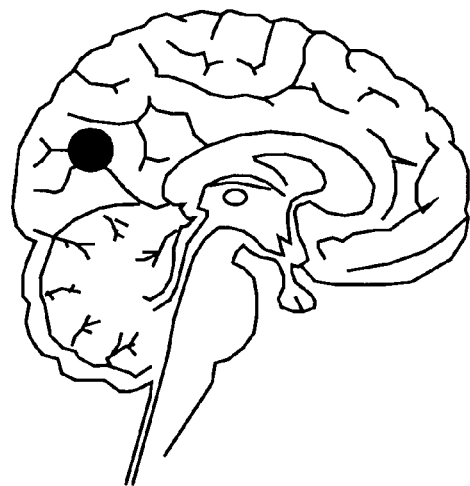
Figure 22B:
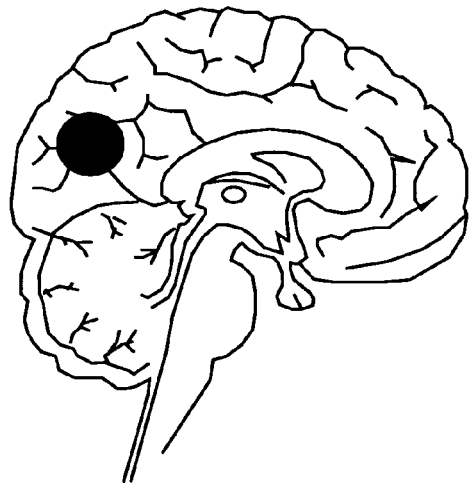
Figure 22C:
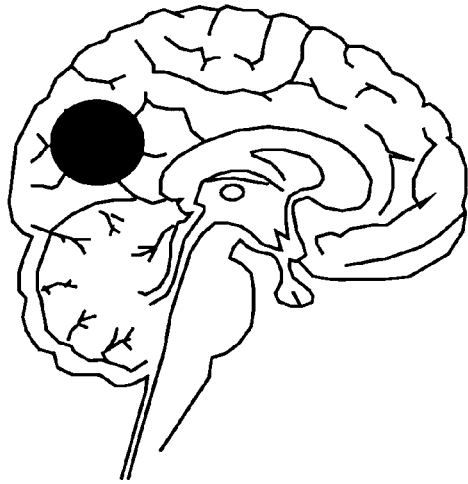

As for the item "size", diagrams indicative of a size (which is specified by a black circle in this case) as shown in FIGS. 22A to 22C may be used instead of a value such as "1-2 cm" when specifying the size of cancer, infarction and the like.

When a plurality of elements belonging to items respectively are associated with other between the items with including diagrams and the like in the support information DB 110, with the entire network information stored in the support information DB 110 being described in RDF, for example, words and information about the drawings can be associated with each other by describing the drawings with an URL while separately memorizing the information themselves about the drawings. In order to incorporate the information about drawings and the like into the information stored in the support information DB 110, the information about drawings and the like needs to be extracted and associated when associating and structuring the elements forming the medical information by analyzing existing medical information.

Such a need is met by performing machine learning by preparing teaching data with additional information about various diagrams to a learning corpus. Using information after the machine learning, existing medical information is analyzed by extracting a word and a phrase and also extracting information about a diagram by a pattern matching method and the like for each item, thereby preparing each structured data that also includes drawings.

Figure 23:
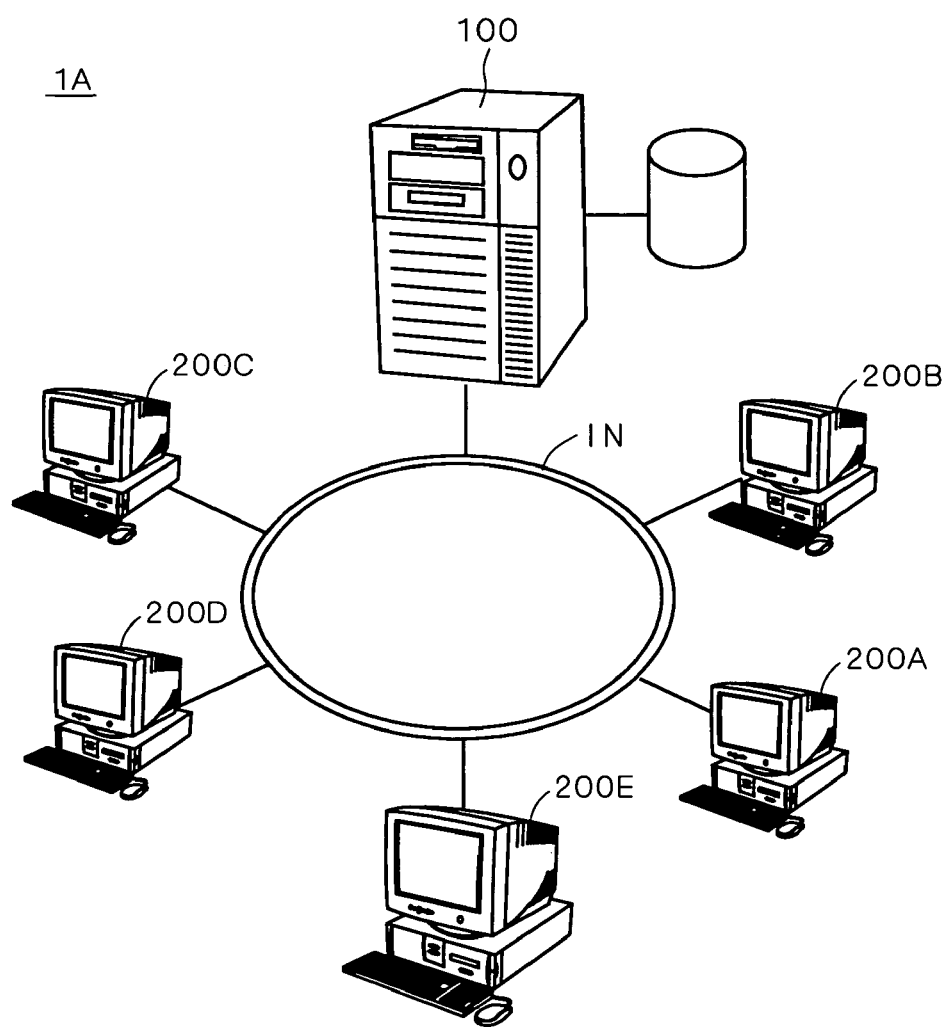
FIG. 23 is a general view of a medical-information presenting system according to a modification.

In the above preferred embodiment, the medical support server 100, the medical-information presenting terminal 200, the terminals 201 to 203, the RIS 300, the blood test information server 400, the discharge summary information server 500, and the electronic chart information server 600 are connected through the network circuit NTW and the like in a hospital in a way that allows mutual data transmission and reception, so that statistical information about the medical information can be obtained at each of the terminals 201 to 203 from the medical support server 100. Alternatively, a medical-information presenting system 1A such as is shown in FIG. 23 may be formed. In this system, the medical support server 100 is provided at a supplier or a specific hospital that supplies support information for medical treatment, and doctors in other hospitals use terminals 200A to 200E like the medical-information presenting terminal 200 to access the medical support server 100 through an internet circuit IN and the like, thereby realizing the support-information presenting operation.

Although the configuration is omitted, the support information DB 110 in the medical support server 100 can be prepared in FIG. 23 in the same way as the above preferred embodiment. In the course of the preparation, the supplier and the like possessing the medical support server 100 may provide service of keeping the medical information of the other hospitals and the like.

Further, while the extracting condition, selecting condition, output target item and the like are specified by operating the operation unit 204 in the above preferred embodiment, these may be specified by recognizing voices from the user.

Further, while the information category is selected on the information-category selecting screen G1 in the above preferred embodiment, the condition-specifying screen G2 may be displayed without selecting an information category. Or the medical-support-information presenting screen G3 may be displayed without selecting an information category and specifying an extracting condition.

While the invention has been shown and described in detail, the foregoing description is in all aspects illustrative and not restrictive. It is therefore understood that numerous modifications and variations can be devised without departing from the scope of the invention.

What is claimed is:

1. An information presentation system comprising:
   a medical support server comprising:
      a memory unit, wherein said memory unit memorizes associated information including network information and count information, said network information listing a plurality of words or phrases with respect to each of a plurality of classifications forming medical information on at least one patient, and associating respective words or phrases belonging to one of said plurality of classifications with respective words or phrases belonging to another of said plurality of classifications, said count information being about a number of combinations of said plurality of words or phrases; and
      a search unit that obtains from said memory unit said network information or partial associated information, including partial network information of said network information and partial count information of said count information corresponding to said partial network information, in response to an operation performed on an operation unit by a user, said partial network information being information associating said respective words or phrases belonging to said one of said plurality of classifications with said respective words or phrases belonging to said another of said plurality of classifications;
   a terminal device connected to said medical support server through a communication line, said terminal device comprising:
      a display unit;
      said operation unit; and
      a control unit, wherein said control unit displays a screen at said display unit based on said network information or said partial network information obtained by said search unit, wherein on said screen, said plurality of words or phrases are listed with respect to each of partial classifications of said plurality of classifications, respective words or phrases belonging to one of said partial classifications are associated with said respective words or phrases belonging to another of said partial classifications by display elements, and at least one residual classification of said plurality of classifications other than said partial classifications is listed, wherein said control unit specifies a word or phrase belonging to at least one classification included in said partial classifications on said screen to thereby specify a selecting condition indicating either of one word or phrase or a combination of words or phrases, said control unit also specifying an output target classification out of at least one of said residual classifications on said screen in response to an operation performed on said operation unit by a user; and
   wherein said search unit receives said selecting condition and said output target classification specified by said control unit, and obtains, as statistical information, at least one of information indicative of a ratio of a word or phrase belonging to said output target classification and information indicative of a distribution of a frequency of appearance of a word or phrase belonging to said output target classification, in a combination of words or phrases in said count information or said partial count information satisfying said selecting condition; and
   said control unit displays said statistical information obtained by said search unit on said screen.

2. The information presentation system according to claim 1, wherein said medical information on at least one patient includes one or more pieces of information including attribute information on at least one patient who has developed symptoms, examination information on at least one patient who has developed said symptoms, examination information on at least one patient who has not developed said symptoms, information indicating treatment, and information indicating a recovery degree, for each case.

3. The information presentation system according to claim 1, wherein said medical information on at least one patient includes information indicative of medical histories of a patient and of one or more persons included in said patient's family.

4. The information presentation system according to claim 1, wherein
   said selecting condition indicates a combination of words or phrases belonging to a plurality of classifications respectively regarding examination information and treatment, and
   said statistical information includes statistical information about development prediction,
   wherein a disk stores executable instructions associated with a distribution unit associated with said information presentation system and operable to distribute information indicative of said selecting condition, said at least one output target classification, and said statistical information about development prediction to predetermined communications equipment.

5. The information presentation system according to claim 1, wherein said plurality of classifications include a classification about at least one of symptom development and a change in condition of said at least one patient.

6. The information presentation system according to claim 1,
   wherein a disk stores executable instructions associated with:
      an information-accepting unit associated with said information presentation system and operable to accept input information, said input information corresponding to association between words or phrases belonging to said plurality of classifications and said plurality of classifications, and
   an information-updating unit associated with said information presentation system and operable to update said associated information database by adding information indicative of said association between said words or phrases belonging to said plurality of classifications and said associated information based on said input information.

7. The information presentation system according to claim 1, wherein
   said selecting condition indicates at least one word or phrase belonging to one or more classifications about a surgical method and treatment,
   said at least one output target classification includes one or more classifications about symptom development of said at least one patient, a period, and cost, and
   said output unit is further operable to output said selecting condition.

8. The information presentation system according to claim 1, wherein
   said output unit is further operable to visibly output a view of network information based on said associated information, said network information comprising a network relationship graph including associations between a plurality of words or phrases belonging to classifications respectively included in said plurality of classifications.

9. The information presentation system according to claim 8, wherein a disk stores executable instructions associated with an information-extracting unit associated with said information presentation system and operable to extract partial associated information corresponding to an extracting condition out of said associated information in response to specification of said extracting condition by a user.

10. The information presentation system according to claim 1, wherein
said associated information includes information that defines hierarchical associations between a plurality of words or phrases belonging to said plurality of classifications respectively.

11. The information presentation system according to claim 1, wherein
said associated information includes information in which one word or phrase belonging to a first classification and two or more words or phrases belonging to a second classification are directly associated between said first and second classifications included in said plurality of classifications.

12. The information presentation system according to claim 1, wherein said associated information includes information described in a Resource Description Framework ("RDF").

13. The information presentation system according to claim 12, further comprising:
a second memory unit operable to store a medical information database, said medical information database storing medical information on a plurality of patients; and
wherein a disk stores executable instructions associated with an information-generating unit associated with said information presentation system and operable to generate said associated information by performing predetermined information processing including language processing on said medical information on a plurality of patients.

14. The information presentation system according to claim 1, wherein
said associated information stores, as a word or phrase belonging to a predetermined classification among said plurality of classifications, statistical information about said predetermined classification.

15. The information presentation system according to claim 1, wherein said statistical information includes statistical information in the mode of at least one of ratio, distribution and dispersion.

16. The information presentation system according to claim 1, wherein said display elements comprise a line on said screen that connects said respective words or phrases belonging to said one of said partial classifications with said respective words or phrases belonging to said another of said partial classifications.

17. A method for controlling a computer to operate as an information presentation system said method comprising:
executing a program via a central processing unit of a computer so that the following processes are performed:
memorizing in a memory unit associated information including network information and count information, said network information listing a plurality of words or phrases with respect to each of a plurality of classifications forming medical information on at least one patient, and associating respective words or phrases belonging to one of said plurality of classifications with respective words or phrases belonging to another of said plurality of classifications, said count information being about a number of combinations of said plurality of words or phrases; and
obtaining from said memory unit via a search unit said network information or partial associated information, including partial network information of said network information and partial count information of said count information corresponding to said partial network information, in response to an operation performed on an operation unit by a user, said partial network information being information associating said respective words or phrases belonging to said one of said plurality of classifications with said respective words or phrases belonging to said another of said plurality of classifications;
displaying a screen at a display unit via a control unit based on said network information or said partial network information obtained by said search unit, wherein on said screen, said plurality of words or phrases are listed with respect to each of partial classifications of said plurality of classifications, respective words or phrases belonging to one of said partial classifications are associated with said respective words or phrases belonging to another of said partial classifications by display elements, and at least one residual classification of said plurality of classifications other than said partial classifications is listed;
having said control unit specify a word or phrase belonging to at least one classification included in said partial classifications on said screen to thereby specify a selecting condition indicating either of one word or phrase or a combination of words or phrases;
having said control unit also specify an output target classification out of at least one of said residual classifications on said screen, in response to an operation performed on said operation unit by a user; and
having said search unit receive said selecting condition and said output target classification specified by said control unit, and obtain, as statistical information, at least one of information indicative of a ratio of a word or phrase belonging to said output target classification and information indicative of a distribution of a frequency of appearance of a word or phrase belonging to said output target classification, in a combination of words or phrases in said count information or said partial count information satisfying said selecting condition; and
having said control unit display said statistical information obtained by said search unit on said screen.

18. The method according to claim 17, wherein said display elements comprise a line on said screen that connects said respective words or phrases belonging to said one of said partial classifications with said respective words or phrases belonging to said another of said partial classifications.

19. A computer software product recorded on a non-transitory computer readable medium for controlling a computer to operate as an information presentation system, said computer executing the computer software product via a central processing unit of a computer so that the following operations are performed:
memorizing in a memory unit associated information including network information and count information, said network information listing a plurality of words or phrases with respect to each of a plurality of classifications forming medical information on at least one patient, and associating respective words or phrases belonging to one of said plurality of classifications with respective words or phrases belonging to another of said plurality of classifications, said count information being about a number of combinations of said plurality of words or phrases; and obtaining from said memory unit via a search unit said network information or partial associated information, including partial network information of said network information and partial count information of said count information corresponding to said partial network information, in response to an operation performed on an operation unit by a user, said partial network information being information associating said respective words or phrases belonging to said one of said plurality of classifications with said respective words or phrases belonging to said another of said plurality of classifications;

displaying on a screen at a display unit via a control unit based on said network information or said partial network information obtained by said search unit, wherein on said screen, said plurality of words or phrases are listed with respect to each of partial classifications of said plurality of classifications, respective words or phrases belonging to one of said partial classifications are associated with said respective words or phrase belonging to another of said partial classifications by display elements, and at least one residual classification of said plurality of classifications other than said partial classifications is listed;

having said control unit specify a word or phrase belonging to at least one classification included in said partial classifications on said screen to thereby specify a selecting condition indicating either of one word or phrase or a combination of words or phrases;

having said control unit also specify an output target classification out of at least one of said residual classifications on said screen, in response to an operation performed on said operation unit by a user; and having said search unit receive said selecting condition and said output target classification specified by said control unit, and obtain, as statistical information, at least one of information indicative of a ratio of a word or phrase belonging to said output target classification and information indicative of a distribution of a frequency of appearance of a word or phrase belonging to said output target classification, in a combination of words or phrases in said count information or said partial count information satisfying said selecting condition; and having said control unit display said statistical information obtained by said search unit on said screen.

20. The computer software product according to claim 19, wherein said display elements comprise a line on said screen that connects said respective words or phrases belonging to said one of said partial classifications with said respective words or phrases belonging to said another of said partial classifications.

* * * * *